United States Patent
Gerwick et al.

(10) Patent No.: US 11,357,817 B2
(45) Date of Patent: Jun. 14, 2022

(54) IMMUNOPROTEASOME INHIBITOR

(71) Applicant: The Regents of the University of California, Oakland, CA (US)

(72) Inventors: William Gerwick, La Jolla, CA (US); Betsaida Bibo Verdugo, San Diego, CA (US); Anthony O'Donoghue, San Diego, CA (US); Jehad Almaliti, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 16/613,582

(22) PCT Filed: May 15, 2018

(86) PCT No.: PCT/US2018/032695
§ 371 (c)(1),
(2) Date: Nov. 14, 2019

(87) PCT Pub. No.: WO2018/213263
PCT Pub. Date: Nov. 22, 2018

(65) Prior Publication Data
US 2020/0078437 A1     Mar. 12, 2020

Related U.S. Application Data

(60) Provisional application No. 62/506,062, filed on May 15, 2017.

(51) Int. Cl.
*A61K 38/06*     (2006.01)
*A61P 33/06*     (2006.01)

(52) U.S. Cl.
CPC .............. *A61K 38/06* (2013.01); *A61P 33/06* (2018.01)

(58) Field of Classification Search
CPC .......... A61K 38/06; A61P 33/06; C07K 5/08; C07K 5/0808; C07K 5/0812; C07K 5/0815; C07K 5/0821; G05F 1/10; H02M 2001/0022; H02M 2001/008; H02M 3/04; H02M 3/08; H02M 3/33592; H02M 3/3378; Y02B 70/10; Y02B 70/1475
See application file for complete search history.

(56) References Cited

U.S. PATENT DOCUMENTS

| | | | |
|---|---|---|---|
| 9,409,944 B2 * | 8/2016 | Gerwick | ................. A61P 35/00 |
| 9,434,761 B2 * | 9/2016 | McMinn | ............ C07K 5/06078 |
| 2006/0088471 A1 | 4/2006 | Bennett et al. | |
| 2007/0293465 A1 | 12/2007 | Shenk et al. | |
| 2014/0100154 A1 | 4/2014 | Phiasivongsa et al. | |
| 2014/0248333 A1 | 9/2014 | Gerwick et al. | |
| 2014/0336106 A1 | 11/2014 | McMinn et al. | |
| 2015/0166601 A1 * | 6/2015 | Morgan | ................. A61P 35/00 |
| | | | 514/19.6 |
| 2016/0031934 A1 | 2/2016 | McMinn et al. | |

FOREIGN PATENT DOCUMENTS

WO     WO2017/066763     *     4/2017     ............. A61K 39/00

OTHER PUBLICATIONS

PCT International Search Report and Written Opinion for PCT Application No. PCT/US2018/032695 dated Jul. 30, 2018 (9 pages).

* cited by examiner

Primary Examiner — Marcela M Cordero Garcia
(74) Attorney, Agent, or Firm — Eversheds Sutherland (US) LLP

(57) ABSTRACT

Methods and pharmaceutical compositions for treating malaria and immune related disorders are provided. The pharmaceutical compositions include an effective amount a carmaphycin B analog that inhibits immunoproteasome activity in a subject.

7 Claims, 6 Drawing Sheets
Specification includes a Sequence Listing.

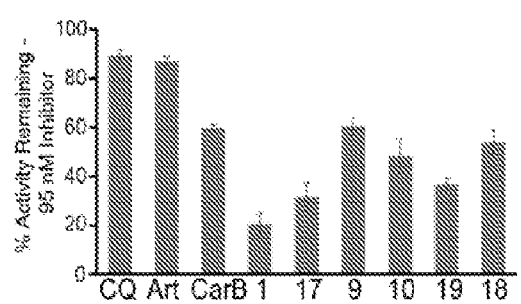
FIGURE 3C
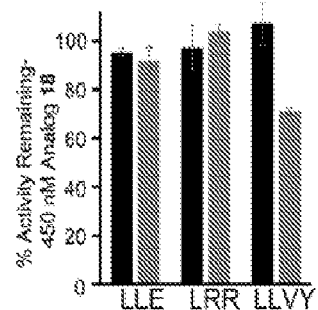
FIGURE 3D
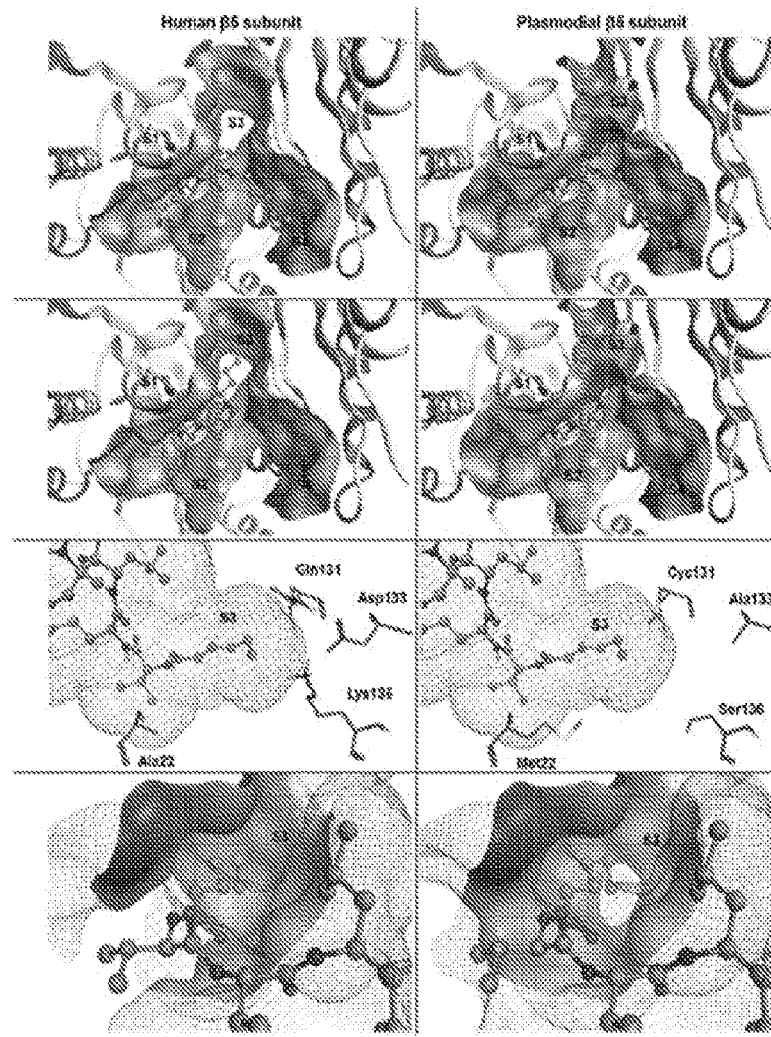
Figure 4A
Figure 4B
Figure 4C
Figure 4D

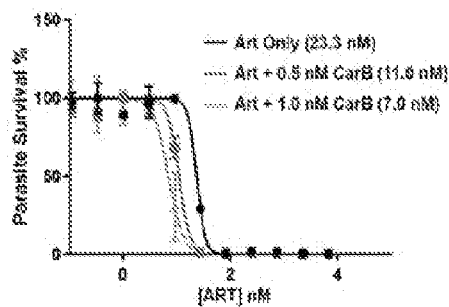
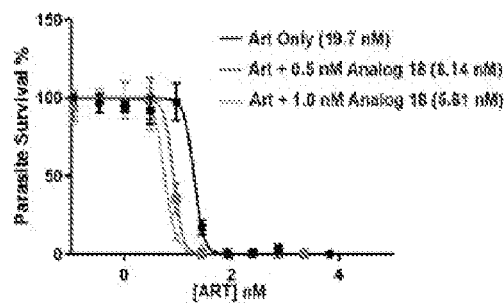
FIGURE 5A  FIGURE 5B
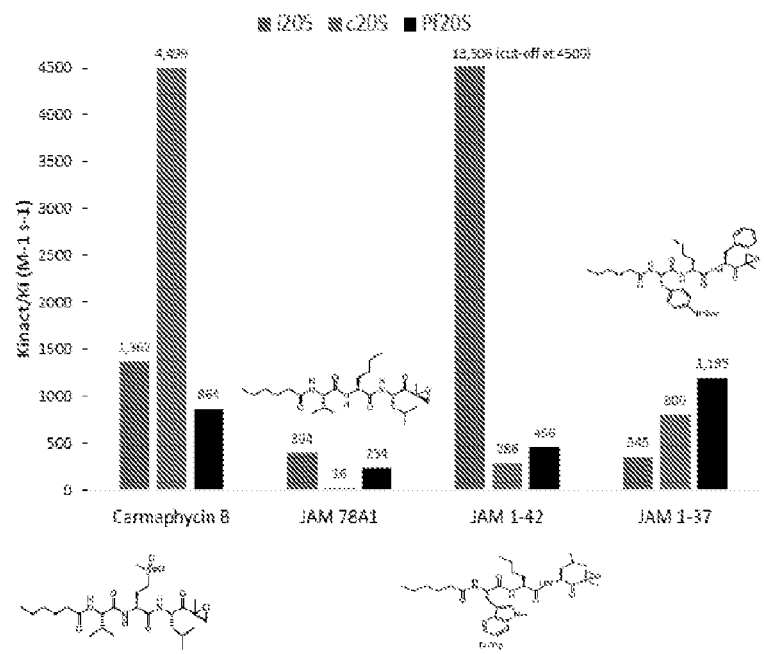
FIGURE 6

IMMUNOPROTEASOME INHIBITOR

CROSS REFERENCE TO RELATED APPLICATIONS

This application claims the priority benefit of PCT/US2018/032695 filed on May 15, 2018 which claims priority benefit to U.S. Provisional Patent Application No. 62/506,062, filed May 15, 2017, the entire contents of which are incorporated by reference.

SEQUENCE LISTING

The instant application contains a Sequence Listing which has been submitted electronically in ASCII format and is hereby incorporated by reference in its entirety. Said ASCII copy, created on Mar. 17, 2021, is named 24978-0523_SL.txt and is 11,990 bytes in size.

FIELD OF THE INVENTION

The present disclosure relates to selective immunoproteasome inhibitor compositions and methods of using the same.

BACKGROUND OF THE INVENTION

The carmaphycins are potent cancer cell toxins that work via inhibition of the mammalian proteasome. There are actually at least two different types of proteasome, one which is 'constitutive' and present in all or most cells, and another that is known as the 'immunoproteasome', which is found predominantly in monocytes and lymphocytes. A more selective immunoproteasome inhibitor would have very beneficial properties for treating inflammation, including rheumatoid arthritis, autoimmune disorders, and cancer.

The proteasome is a multicatalytic complex that fulfills a critical role in cellular homeostasis through the regulated degradation of proteins, producing small peptides. Such turnover affects key regulatory components in cell signaling, clearance of mutated or misfolded proteins, as well as antigen presentation.[1] Proteasomes are barrel-shaped structures composed of four stacked heptameric rings. The two outer rings, containing the α-subunits, act as binding sites for regulatory complexes (e.g., 19S, 11S, and PA200) that modulate the access of cytosolic proteins into the proteasome inner chamber.[2] The proteolytic activity of the proteasome is concentrated in the two inner rings, each of which contains three catalytic subunits (β1, β2, and β5). These active sites have been traditionally referred to as the "caspase-," "trypsin-," and "chymotrypsin-like" subunits, respectively, based on their general substrate specificity preferences.[3]

In addition to the constitutive proteasome (c20S), which is expressed in almost all cell types, three additional tissue-specific proteasome isoforms have been identified in humans. The immunoproteasome (i20S) is constitutively expressed in hematopoietic cells. The i20S has been extensively investigated in recent years due to its role in antigen presentation. Pro-inflammatory signals trigger increased levels of the i20S, which has altered catalytic subunits—LMP2 (iβ1), MECL-1 (iβ2), and LMP7 (iβ5).[6-8] Initial evidence suggests that the i20S catalytic subunits show an enhanced ability to generate antigenic peptides with specific C-terminal anchor residues that are bound and displayed by major histocompatibility complex (MHC) class I molecules. Mice completely lacking in immunoproteasomes display an antigen repertoire that differs by 50 percent from wild-type mice and results in transplant rejection.[9] Therefore, differences in i20S substrate specificity are critical for the immune response.[10]

Deregulation of the proteasome, as occurs in the context of cancer, leads to the proteolysis of multiple regulatory proteins, thereby accelerating mitosis and favoring cancer progression.[11] Indeed, proteasome inhibitors were initially developed as anti-cancer therapeutic agents due to their capacity to induce apoptosis in proliferating cells, while also inhibiting angiogenesis.[12,13] Bortezomib (Velcade®), a reversible boronic acid-based inhibitor that primarily targets the chymotrypsin-like subunits, provided clinical validation of the proteasome as a therapeutic target in multiple myeloma.[11] The second-generation proteasome inhibitor carfilzomib (CFZ; Kyprolis® or PR-171) uses an irreversible epoxyketone warhead and shows reduced off-targets while circumventing resistance against bortezomib.[14,15] Although highly effective, these FDA-approved drugs lack isoform selectivity.[16-18] Therefore, much recent effort has been dedicated toward the development of LMP7- and β5-selective inhibitors in the interest of limiting collateral toxicity. The recently identified epoxyketone inhibitor, ONX 0914 (PR-957), preferentially inhibits the LMP7 subunit. This inhibitor was able to induce an anti-inflammatory response in a rheumatoid arthritis mouse model at a significantly lower dose than bortezomib and CFZ, suggesting a wider therapeutic window for autoimmune disorder treatment.[19] Other epoxyketone inhibitors, such as PR-825, have been developed that hold treatment promise through preferential inhibition of the β5 subunit.[19]

Beyond cancer, malaria continues to be a major global health challenge despite extensive public health interventions (1), resulting in millions of infections per year and 438,000 deaths, mostly children under the age of 5 years. Furthermore, as the efficacy of artemisinin combination therapies continue to wane due to the emergence of drug resistant strains (2, 3), it is feared that malaria will continue to expand and cause significant hardships worldwide. This onset of drug resistance highlights the urgent need for developing new and potent antimalarial compounds with novel mechanisms of action. In particular, there has been a significant focus on identifying compounds which possess transmission blocking or prophylactic activity, rather than the traditional focus on relief of clinical symptoms due to blood-stage infection. In the last 5-10 years, numerous phenotypic screens have been undertaken, which have identified several novel antimalarial compounds (4). More recently, as part of the effort to increase the utility of those screens, there has been a search for increased chemical diversity in a variety of parasitic species, such as through the introduction of the Global Health Chemical Diversity (GHDL) and Diversity-oriented Synthesis (DOS) libraries (5, 6), to increase the chance of identifying novel antimalarial chemotypes which can affect multiple different stages of parasite development.

One often utilized source of chemical diversity are natural products, which have been successful in screening programs as they often possess distinct chemical structures that have proven to be a valuable resource for anti-cancer, anti-hypertension and anti-microbial compounds (7). Several of the most prominent antimalarial compounds, including quinine and artemisinin were isolated from natural sources (8).

Due to its synergy with the mechanism of action of artemisinin, the *plasmodium* proteasome is an extremely promising drug target for the next-generation of antimalarial chemicals. Unfortunately, the highly conserved nature of the proteasome across species has led to significant problems with host-cell toxicity in currently utilized proteasome inhibitors.

Carmaphycin B and a related compound carmaphycin A, were originally isolated from extracts derived from the Curacao cyanobacterium Symploca sp. (9). They are tripeptide molecules, capped on the amino terminus with an N-hexanoyl group and an α,β-epoxyketone group on the carboxyl terminus. Carmaphycin B consists of L-valine, L-methionine sulfone and L-leucine while carmaphycin A has L-methionine sulfoxide instead of the methionine sulfone. Both compounds elicit a strong cytotoxic effect on a human lung adenocarcinoma and a colon cancer cell line (9). This cytotoxic effect is likely due to targeting of the constitutive proteasome, as has been demonstrated with the α,β-epoxyketone inhibitor, carfilzomib. Carfilzomib is an approved drug for treatment of refractory or relapsed multiple myeloma. Carfilzomib also kills asexual blood stage $P.$ $falciparum$ (10) and can strongly synergize ART activity (11). In addition, analogs of carfilzomib have been shown to have oral bioavailability (12), a critical feature for antimalarial compounds. However, the concentration of carfilzomib required for effective treatment of malaria would be toxic to host cells, and this lack of specificity has largely rendered it unusable from an anti-microbial perspective.

A peptide epoxyketone inhibitor with reduced toxicity to $Plasmodium$ and host cells was identified in a screen of carfilzomib analogs. This compound had sufficient selectivity to reduce parasite load in $P.$ $berghei$ infected mice without host toxicity but was unable to clear parasitemia (10). These studies confirmed that antimalarial proteasome inhibitors with low host cytotoxicity can be designed, however a significant improvement in anti-malarial potency is needed.

SUMMARY OF THE INVENTION

The present disclosure provides a new class of compounds derived from carmaphycin B, termed 78A1 analogs or carmaphycin B analogs. These compounds are $Plasmodium$ proteasome inhibitors based on the carmaphycin B scaffold. The compounds have potent antimalarial activity (e.g. asexual and transmission-blocking activity) combined with dramatically reduced host cytotoxicity when compared to other proteasome inhibitors. Thus, the compounds are potent inhibitors against all blood stages of malaria infection (e.g. have potent antimalarial activity against the sexual and asexual lifecycle stages). The compounds also have chemical structural features that serve to enhance antimalarial specificity. The compounds more generally have potent anti-proliferative and anti-infective activity.

One representative and particularly promising compound, JAM 1-42 (Analog 18), is exquisitely selective as an inhibitor of the immunoproteasome (47-fold selective inhibition of the immunoproteasome over the constitutive proteasome). JAM 1-42 (Analog 18) is the most selective immunoproteasome inhibitor produced to date. The only other reported selective inhibitor in the literature, PR-957, only shows between 20- to 40-fold selective inhibition as reported in an article by Muchamuel. JAM 1-42 (Analog 18) has a 100-fold wider therapeutic window than carmaphycin B and consists of the substitutions of D-valine for L-valine, and norleucine for methionine sulfone. This compound retains potent antimalarial efficacy in cell based assays against both asexual blood stages and gametocytes, and strongly inhibits the activity of the isolated $Plasmodium$ proteasome in vitro.

More generally, a combination of in silico molecular docking and in vitro directed evolution in a well-characterized drug-sensitive yeast model ($S.$ $cerevisiae$) confirmed that the activity of the carmaphycin B analogs is due to specific inhibition of the β5 subunit of the proteasome (the compounds target the β5 subunit of the proteasome). Molecular modeling of these inhibitors with the β5-subunit of the human versus parasite proteasome determined that subtle structural differences in the β5-subunit active site permit this selectivity. These studies were validated using in vitro inhibition assays with proteasomes isolated from $Plasmodium$ $falciparum$. The studies conclusively demonstrated that the toxicity of immunoproteasome inhibitors to human cells (e.g. carmaphycin B is toxic to mammalian cells) can be dramatically reduced while still maintaining potent antimicrobial activity. The synthesized chemical analogs reduce host cell toxicity while maintaining dual stage antimalarial activity and proteasome inhibition.

In embodiments, the invention provides pharmaceutical compositions and methods for treating a disease comprising administering to a subject in need thereof an effective amount of a composition comprising a carmaphycin B analog. In embodiments, the carmaphycin B analog has methionine sulfone replaced with norleucine in position P2. In embodiments, the carmaphycin B analog has decreased cytotoxicity and increased selectivity for inhibiting immunoproteasome activity over constitutive proteasome activity as compared to carmaphycin B. In embodiments, the subject is a human. In embodiments, the disease is for example malaria, an immune related disorder, cancer, or rheumatoid arthritis.

In embodiments, the carmaphycin B analog has L-Val replaced with D-Val or D-Trp in position P3. In embodiments, the carmaphycin B analog is Analog 18: (S)-2-((R)-2-hexanamido-3-methylbutanamido)-N—((S)-4-methyl-1-((R)-2-methyloxiran-2-yl)-1-oxopentan-2-yl)hexanamide.
In embodiments, the carmaphycin B analog is Analog 19: (S)-2-((R)-2-hexanamido-3-(1H-indol-3-yl)propanamido)-N—((S)-4-methyl-1-((R)-2-methyloxiran-2-yl)-1-oxopentan-2-yl)hexanamide. In embodiments, the carmaphycin B analog is Analog 1: (S)-2-((S)-2-hexanamido-3-methylbutanamido)-N—((S)-4-methyl-1-((R)-2-methyloxiran-2-yl)-1-oxopentan-2-yl)hexanamide.

In embodiments, the carmaphycin B analog specifically inhibits a β5 subunit of the immunoproteasome. In embodiments, the carmaphycin B analog has improved specificity for $P.$ $falciparum$ as compared to carmaphycin B.

BRIEF DESCRIPTION OF THE DRAWINGS

FIG. 2A: binding mode of carmaphycin B in the yeast wild type structure based on molecular docking of carmaphycin B into the yeast 20S proteasome:carmaphycin A co-crystal structure (PDB ID 4HRD). FIG. 2B: modeling of the mutation of residue Met45 to Ile45 leads to a steric clash between the P1 leucine and the mutated Ile45 residue. The mutated Ile45 residue penetrates the interaction surface of carmaphycin B preventing the efficient binding of the ligand. The interaction surface is color coded according to the lipophilicity of the molecule with hydrophobic (blue) and lipophilic (red) areas.

FIGS. 3A-3D show an inhibition of the Human (black bars) and *Plasmodium proteasome* (gray bars) by Carmaphycin B and 6 plasmodium specific analogs. FIG. 3A: activity against the 3 enzymatic subunits of Pf20S and the c20S. FIG. 3B: potency against c20S for carmaphycin B and the indicated compounds. FIG. 3C: on-target studies with the synchronized trophozoite parasites for the indicated analogs. FIG. 3D: Analog 18 compound activity against the 3 enzymatic subunits of Pf20S and the c20S. FIGS. 3A-3D disclose "LLVY" as SEQ ID NO: 1.

FIGS. 4A-4D show a schematic representation of carmaphycin B (blue) and analog 18 (orange) in ball and stick representation bound to the human 20S proteasome β5 binding pocket (left, PDB ID 4R67) and the *P. falciparum* 20S proteasome β5 binding pocket of the homology model homPf_β5 (right). The molecular surface of the protein binding pocket is shown with hydrophilic (blue) and hydrophobic (red) surface areas. FIG. 4A: Carmaphycin B bound to the β5 subunit. FIG. 4B: Analog 18 bound in the switched conformation. FIG. 4C: Analog 18 binding conformation in the S3 protein pocket. The residues that were identified to be associated with the preferred binding of analog 18 towards the *plasmodium* 20S proteasome β5 subunit are shown in grey. The interaction surface of the inhibitor analog 18 is color coded according to the lipophilicity of the molecule with hydrophilic (blue) and hydrophobic (red) areas. FIG. 4D: Analog 18 binding conformation in the S3 protein pocket. The molecular surface of the S3 binding pocket is shown as solid surface areas whereas the whole binding pocket is shown as line representation.

FIGS. 5A-5B show synergistic activity of artemisinin with sub IC50 doses of carmaphycin B and analog 18. FIG. 5A: Artemisinin $IC_{50}$, as determined by 72 hour SYBR green assay, of Dd2 parasites when co-treated with the indicated concentrations of carmaphycin B. FIG. 5B: Artemisinin $IC_{50}$, as determined by 72 hour SYBR green assay, of Dd2 parasites when co-treated with the indicated concentrations of Analog 18.

FIG. 6. JAM 1-42 (Analog 18) is exquisitely selective as an inhibitor of the immunoproteasome (47-fold selective inhibition of the immunoproteasome over the constitutive proteasome).

FIGS. 9A-9B show multiple sequence alignment of the (A) β5 and (B) β6 proteins chains of the human 20S proteasome (PDB ID 4R67 chain L and M), the parasitic 20S proteasome (PDB ID 5FMG chain L and M) and the yeast 20S proteasome (PDB ID 4HRD chain K and L). Residue labeling is according to PDB code 4R67. The residues in red are catalytic residues and the residues in blue were identified as residue substitutions in the Pf 20S proteasome model that are associated with the preferred binding of Analog 18 towards the *plasmodium* 20S proteasome β5 subunit (Table 7). The methionine residue (green) is replaced by isoleucine in the carmaphycin resistant yeast mutant strain. FIG. 9A discloses SEQ ID NOS 2-4, respectively, in order of appearance. FIG. 9B discloses SEQ ID NOS 5-7 respectively, in order of appearance.

DETAILED DESCRIPTION OF THE INVENTION

Figure 1:
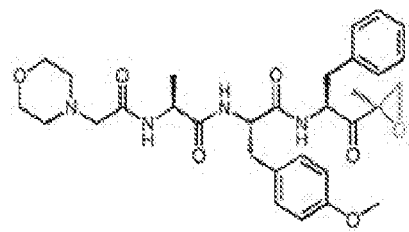
FIG. 1 shows the structure of ONX 0914 (PR-957), an epoxyketone inhibitor, the most selective i20S inhibitor known in the literature.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Pharmaceutically active: The term "pharmaceutically active" as used herein refers to the beneficial biological activity of a substance on living matter and, in particular, on cells and tissues of the human body. A "pharmaceutically active agent" or "drug" is a substance that is pharmaceutically active and a "pharmaceutically active ingredient" (API) is the pharmaceutically active substance in a drug. As used herein, pharmaceutically active agents include synthetic or naturally occurring small molecule drugs and more complex biological molecules.

Pharmaceutically acceptable: The term "pharmaceutically acceptable" as used herein means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

Pharmaceutically acceptable salt: The term "pharmaceutically acceptable salt" as used herein refers to acid addition salts or base addition salts of compounds, such as a carmaphycin B analog, in the present disclosure. A pharmaceutically acceptable salt is any salt which retains the activity of the parent compound and does not impart any deleterious or undesirable effect on a subject to whom it is administered and in the context in which it is administered. Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use, Wiley-VCH; Verlag Helvetica Chimica Acta, Zürich, 2002; Berge et al., J Pharm. Sci. 66: 1, 1977). In some embodiments, a "pharmaceutically acceptable salt" is intended to mean a salt of a free acid or base of a compound represented herein that is non-toxic, biologically tolerable, or otherwise biologically suitable for administration to the subject. See, generally, Berge, et al., J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates.

Pharmaceutically acceptable carrier: The terms "pharmaceutically acceptable carrier" as used herein refers to an excipient, diluent, preservative, solubilizer, emulsifier, adjuvant, and/or vehicle with which a compound, such as a carmaphycin B analog, is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy, 20th ed., (Lippincott, Williams & Wilkins 2003). Except insofar as any conventional media or agent is incompatible with the active compound, such use in the compositions is contemplated.

As used herein, "preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition.

As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition. More specific embodiments are included in the sections below. In some embodiments, the term "therapeutically effective amount" or "effective amount" refers to an amount of a therapeutic agent that when administered alone or in combination with an additional therapeutic agent to a cell, tissue, or subject is effective to prevent or ameliorate the disease or condition such as an infection or the progression of the disease or condition. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent, the subject shows observable and/or measurable reduction in or absence of one or more signs and symptoms of the particular disease. Reduction of the signs or symptoms of a disease may also be felt by the patient. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

The terms "inhibit" or "inhibiting" refer to slowing, reducing or preventing a particular activity or function, such as that of an enzyme or multicatalytic complex, including that of an immunoproteasome.

The term "combination" refers to either a fixed combination in one dosage unit form, or a kit of parts for the combined administration where a compound and a combination partner (e.g., another drug as explained below, also referred to as "therapeutic agent" or "co-agent") may be administered independently at the same time or separately within time intervals, especially where these time intervals allow that the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a compound and a combination partner, are both administered to a patient simultaneously in the form of a single entity or dosage. The term "non-fixed combination" means that the active ingredients, e.g., a compound and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

The pharmaceutical compositions comprising a carmaphycin B analog, alone or in combination with other active ingredient(s), described herein may further comprise one or more pharmaceutically-acceptable excipients. A pharmaceutically-acceptable excipient is a substance that is non-toxic and otherwise biologically suitable for administration to a subject. Such excipients facilitate administration of a carmaphycin B analog, alone or in combination with other active ingredient(s), described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the various embodiments are sterile compositions. Pharmaceutical compositions may be prepared using compounding techniques known or that become available to those skilled in the art.

Sterile compositions are within the present disclosure, including compositions that are in accord with national and local regulations governing such compositions.

The pharmaceutical compositions and a carmaphycin B analog, alone or in combination with other active ingredient(s), described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. A carmaphycin B analog, alone or in combination with other active ingredient(s), described herein, and preferably in the form of a pharmaceutical composition, may be administered by a suitable route of delivery, such as oral, parenteral, rectal, nasal, topical, or ocular routes, or by inhalation. In some embodiments, the compositions are formulated for intravenous or oral administration.

For oral administration, a carmaphycin B analog, alone or in combination with another active ingredient, may be provided in a solid form, such as a tablet or capsule, or as a solution, emulsion, or suspension. To prepare the oral compositions, a carmaphycin B analog, alone or in combination with other active ingredient(s), may be formulated to yield a dosage of, e.g., from about 0.01 to about 50 mg/kg daily, or from about 0.05 to about 20 mg/kg daily, or from about 0.1 to about 10 mg/kg daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compositions may be formulated for rectal administration as a suppository. For parenteral use, including intravenous, intramuscular, intraperitoneal, intranasal, or subcutaneous routes, a carmaphycin B analog, alone or in combination with other active ingredient(s), may be provided in sterile aqueous solutions or suspensions, buffered to an appropriate pH and isotonicity or in parenterally acceptable oil. Suitable aqueous vehicles can include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For nasal, inhaled, or oral administration, a carmaphycin B analog, alone or in combination with other active ingredient(s), may be administered using, for example, a spray formulation also containing a suitable carrier.

For topical applications, a carmaphycin B analog, alone or in combination with other active ingredient(s), are preferably formulated as creams or ointments or a similar vehicle suitable for topical administration. For topical administration, a carmaphycin B analog, alone or in combination with other active ingredient(s), may be mixed with a pharmaceutical carrier at a concentration of about 0.1% to about 10% of drug to vehicle. Another mode of administering a carmaphycin B analog, alone or in combination with other active ingredient(s), may utilize a patch formulation to effect transdermal delivery.

In certain embodiments, the present disclosure provides pharmaceutical compositions comprising a carmaphycin B analog, alone or in combination with other active ingredient(s), and methylcellulose. In certain embodiments, methylcellulose is in a suspension of about 0.1, 0.2, 0.3, 0.4, or 0.5 to about 1%. In certain embodiments, methylcellulose is in a suspension of about 0.1 to about 0.5, 0.6, 0.7, 0.8, 0.9, or 1%. In certain embodiments, methylcellulose is in a suspension of about 0.1 to about 1%. In certain embodiments, methylcellulose is in a suspension of about 0.1, 0.2, 0.3, 0.4, 0.5, 0.6, 0.7, 0.8, 0.8, or 1%. In certain embodiments, methylcellulose is in a suspension of about 0.5%.

One of ordinary skill in the art may modify the formulations within the teachings of the specification to provide numerous formulations for a particular route of administration. In particular, a carmaphycin B analog, alone or in combination with other active ingredient(s), may be modified to render them more soluble in water or other vehicle. It is also well within the ordinary skill of the art to modify the route of administration and dosage regimen of a particular carmaphycin B analog, alone or in combination with other active ingredient(s), in order to manage the pharmacokinetics of the present compounds for maximum beneficial effect in a patient.

As used herein, a subject in need refers to an animal, a non-human mammal or a human. As used herein, "animals" include a pet, a farm animal, an economic animal, a sport animal and an experimental animal, such as a cat, a dog, a horse, a cow, an ox, a pig, a donkey, a sheep, a lamb, a goat, a mouse, a rabbit, a chicken, a duck, a goose, a primate, including a monkey and a chimpanzee.

Other objects, advantages and features of the present invention will become apparent from the following specification taken in conjunction with the accompanying drawings.

Examples

Results

Target Confirmation Through In Vitro Directed Evolution in Yeast

In previous work, biochemical evidence that carmaphycin B inhibits the β5 subunit of the 20S yeast proteasome was shown (9). In order to confirm that the cellular mechanism of action of carmaphycin B is through direct binding to the β5 subunit and determine residues important for interaction, directed evolution in yeast followed by whole genome sequencing was used. This approach has been used successfully to uncover the molecular targets of antiparasitic compounds and helped to determine amino acids crucial for a given target-compound pair (13, 14). Directed evolution was performed by exposing a drug-sensitive S. cerevisiae strain, lacking 16 multidrug ABC-transporter export pumps ($ABC_{16}$-Monster strain; GM) (15), to concentrations of carmaphycin B exceeding the $IC_{50}$ determined for the parental strain. Three carmaphycin B-resistant clones, termed lineage 1, 2 and 3 were isolated, with >6-, 2.2-, and >4-fold resistance when compared to the parental strain (Table S1). The genetic basis of resistance was determined by whole-genome sequencing of the resistant lineages with more than 40-fold coverage (Table S2). The resulting sequences were compared to those of the parental-strain (S288c) reference genome and variants present only in the evolved lines were identified (Table S3).

In each of the three lineages, 9, 4 and 15 single nucleotide variants were detected. In the second resistant clone (lineage 2), a nonsynonymous single-nucleotide change in the PRE2 gene was identified that resulted in a M120I change in the β5 subunit of the 20S proteasome, the putative target of carmaphycin B. The β5 subunit is synthesized as a pro-protein and residue M120I corresponds to M45I in the mature protein. This same mutation has been identified in the β5 subunit of human cell lines after long-term exposure to high doses bortezomib, a proteasome inhibitor used for treatment of multiple myeloma (16). The two other resistant clones have mutations in genes whose products are involved in the ubiquitin pathway (lineage 1: SNT2 and lineage 3: UBP7 and UBP3) (17) and could represent compensatory mutations leading to resistance to carmaphycin B. None of the three lineages contained insertions or deletions relative to the parental strain. Therefore, the available evidence obtained through genetic means further supports that carmaphycin B targets the β5 subunit of the proteasome and that a single amino acid substitution abolishes this interaction.

Molecular Docking Elucidates Target-Compound Interaction

Figure 2A:
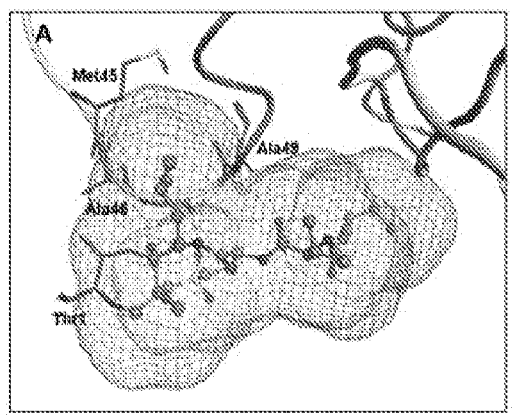
FIGS. 2A-2B show a binding Mode of Carmaphycin B in the $Saccharomyces$ $cerevisiae$ 20S proteasome β5 subunit.
Figure 2B:
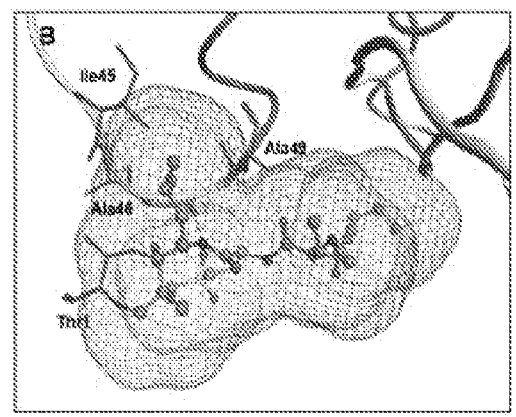

To better understand how the M45I mutation confers carmaphycin B resistance, the crystal structure of the yeast 20S proteasome in complex with carmaphycin A (PDB ID 4HRD) was used for protein engineering in Molecular Operating Environment (MOE) to obtain the model 4HRD-M45I for the mutated β5 subunit (PDB ID 4HRD chain K) (18). Comparison of the mutant and wild-type protein structures shows that the mutation does not trigger apparent changes in the overall protein folding, but rather, influences the direct contact between the ligand and the protein. Detailed analysis of the 4HRD-M45I model suggests that a mutation of Met45 to Ile45 leads to a constriction of the S1 pocket and therefore sterically hinders binding of the inhibitor (FIGS. 2A-2B), and therefore explains how this mutation confers resistance to carmaphycin B and confirms the importance of the M45 residue for target-compound interaction (18, 19).

Carmaphycin B Exhibits Potent Sexual and Asexual Antimalarial Activity

Previous studies on epoxyketone containing compounds such as epoxomicin and carfilzomib, have shown that they possess potent antiprotozoal (20) and antimalarial activity against asexual (10, 21), and sexual blood stages (22). Based on its structural similarity, the activity of carmaphycin B against the asexual blood stage of P. falciparum was evaluated. The natural product was found to possess potent asexual blood stage activity, with an IC50 of 4.1 nM±0.17 as measured by 72 hour SYBR green assay (Table 1), but also exhibits potent activity against the liver-stage (61.6 nM±11) and Stage V gametocytes (160 nM±24).

TABLE 1

Structure and Antimalarial Activity of Carmaphycin B

| Compound Name | Compound Structure | P. falciparum Dd2 $IC_{50}$ (nM) | P. berghei $IC_{50}$ (nM) | P.f. Stage V Gametocyte $EC_{50}$ (nM) |
|---|---|---|---|---|
| Carmaphycin B | 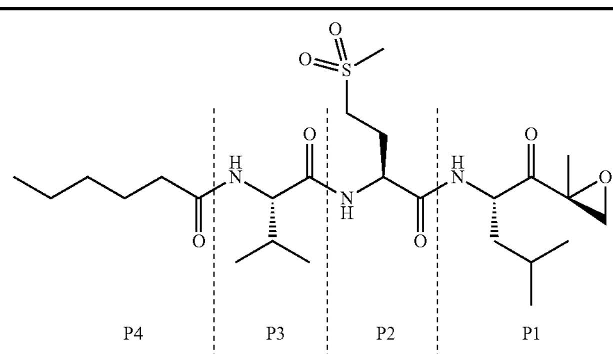 | 4.1 ± 0.17 | 61.6 ± 11 | 160 ± 24 |

Several proteasome inhibitors have also been reported with antimalarial activity but because the 20S proteasome is highly conserved target, many are also cytotoxic to human cells (23). Similarly, carmaphycin B also exhibits significant cytotoxicity against HepG2 cells with $IC_{50}$ of 12.6 nM). Li and colleagues attempted to resolve this problem by using substrate specificity information to design a proteasome inhibitor that is 247-fold more selective against *P. falciparum* trophozoites when compared to human fibroblasts. This selective inhibitor, comprised of a tripeptide with a C-terminal vinyl-sulfone reactive group (WLL-vs), irreversibly targets the active site threonine residue of the β5 subunit (24). Unfortunately, peptide vinyl sulfone inhibitors are additionally known to target several human cysteine proteases that are ubiquitously expressed in human cells (25), leading to potential concerns about off-target specificity. Therefore, the present disclosure focused its efforts on the exquisite specificity of the epoxyketone reactive group for threonine residues to develop proteasome inhibitors with improved selectivity for the *P. falciparum* 20S proteasome.

Carmaphycin B (Table 1) is divided into 4 structural subunits; the leucine epoxyketone (EK) (P1), the methionine sulfone (P2), valine (P3) and hexanoic acid (P4) moieties. The goal of the present disclosure was to design chemical analogs consisting of modifications at P1, P2 and P3 that retain potent antimalarial activity but increased specificity. A convergent, flexible and scalable synthetic procedure that avoids racemization, a common problem in the synthesis of peptide-like structures, was therefore utilized.

Carmaphycin B and 20 synthetic analogs were assayed for their biological activity against *P. falciparum* and HepG2 cells with the goal of identifying modifications that lead to an increase in the selectivity index relative to carmaphycin B (Table 2). For compound 1, the methionine sulfone in the P2 position was changed to norleucine residue, in order to explore the importance of a hydrogen bond at this position. Norleucine was chosen because of its similarity in length and flexibility to methionine sulfone. This replacement decreased the cytotoxic activity of carmaphycin B and resulted in a 10-fold increase in selectivity. With compound 1 as a starting point, two groups of carmaphycin analogs were designed.

The first group of analogs contained a series of P3 side chains of increasing size: L-phenylalanine (analog 2), 3-(4-pyridyl)-L-alanine (L-Pyr-Ala) (analog 3), 4-amino-L-phenylalanine (L-amino-Phe) (analog 4), 4-(Boc-amino)-L-phenylalanine (analog 5) (L-Boc-Phe), and L-tryptophan (analog 6). None of these compounds had improved selectivity when compared to analog 1. The second group of analogs was synthesized using the same selection of P3 amino acids as the first group but substituting L-phenylalanine instead of the original L-leucine residue in the P1 position (analogs 7-11). In a previous study, the *Plasmodium* proteasome showed a clear preference for phenylalanine at the P1 position (24). Correspondingly, most compounds with L-Phe at P1 showed an increased selectivity index compared to their L-Leu counterparts. While several of these analogs, particularly analogs 9 and 10, demonstrated increased selectivity, these analogs showed reduced antimalarial potency relative to analog 1 and therefore were not pursued further. A third group of six analogs, 12-17, was designed to explore the contribution of bulkier P2 residues in combination with similarly sized P3 residues introduced previously. Unfortunately, none of these 6 analogs demonstrated a better combination of potency and selectivity relative to analog 1, and were therefore not studied in more detail.

For the last group of analogs (18-20), the effect of D-amino acids at the P3 position was examined. In previous studies on specific inhibitors of human immunoproteasomes, it has been shown that D-amino acids can have a strong effect on the overall binding mode of the compound (26). The L-Val of analog 1 was therefore replaced with D-Val (analog 18), D-Trp (analog 19), and D-Pyr-Ala (analog 20) in the P3 position. Remarkably, analogs 18 and 19 showed up to 100-fold reduced toxicity together with higher antimalarial potency, resulting in a 100-fold increase in selectivity for analogs 18 and 19. Overall, the most promising derivative, 18, shows a 123-fold increase in selectivity index compared to the natural product carmaphycin B while at the same time retaining its potent anti-gametocyte activity, with an $IC_{50}$ against stage V gametocytes of 130 nM.

Table 2 illustrates carmaphycin B and analogs 1-20 along with their *P. falciparum* asexual blood stage activity and cytotoxicity towards HepG2 cells and the selectivity index (comparing the *P. falciparum* activity versus HepG2 activity. The residue in the chemical structure that changes compared to the previous group of analogs is colored in red.

TABLE 2 illustrates carmaphycin B and analogs 1-20

| Comp # | Structure | P3 | P2 | P1 | *P. falciparum* Dd2 IC50 [nM] | HepG2 IC50 [nM] | Selectivity Index |
|---|---|---|---|---|---|---|---|
| Carmaphycin B | 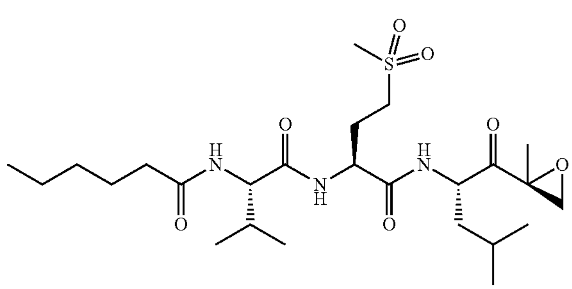 [SMILES: CCCCCC(=O)N[C@H](C(=O)N[C@@H](CCS(C)(=O)=O)C(=O)N[C@@H](CC(C)C)C(=O)[C@@]1(C)CO1)C(C)C] | L-Val | L-Met-Ox | L-Leu-EK | 4.10 ± 0.17 | 12.6 ± 1.40 | 3.07 |

TABLE 2-continued illustrates carmaphycin B and analogs 1-20

| Comp # | Structure | P3 | P2 | P1 | P. falciparum Dd2 IC50 [nM] | HepG2 IC50 [nM] | Selectivity Index |
|---|---|---|---|---|---|---|---|
| 1 | 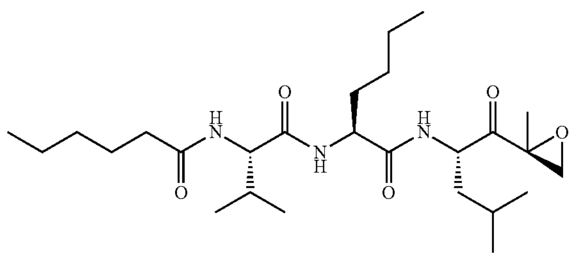 [SMILES: CCCCCC(=O)N[C@H](C(=O)N[C@@H](CCCC)C(=O)N[C@@H](CC(C)C)C(=O)[C@@]1(C)CO1)C(C)C] | L-Val | L-Nle | L-Leu-EK | 4.11 ± 0.077 | 134 ± 86.7 | 33.33 |
| 2 | 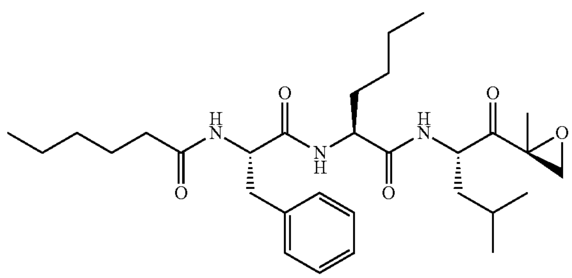 [SMILES: CCCCCC(=O)N[C@@H](Cc1ccccc1)C(=O)N[C@@H](CCCC)C(=O)N[C@@H](CC(C)C)C(=O)[C@@]1(C)CO1] | L-Phe | L-Nle | L-Leu-EK | 4.04 ± 0.759 | 22.7 ± 8.42 | 5.62 |
| 3 | 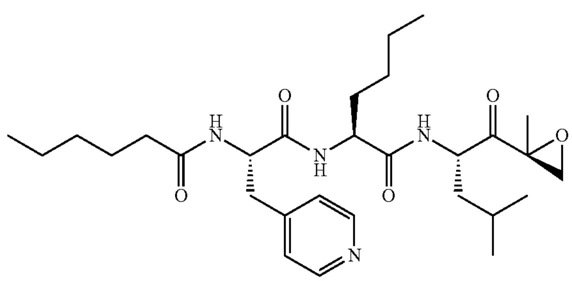 [SMILES: CCCCCC(=O)N[C@@H](Cc1ccncc1)C(=O)N[C@@H](CCCC)C(=O)N[C@@H](CC(C)C)C(=O)[C@@]1(C)CO1] | L-Pyr-Ala | L-Nle | L-Leu-EK | 3.28 ± 0.674 | <0.283 | 0.09 |
| 4 | 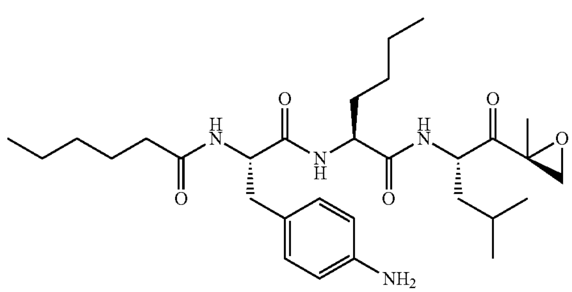 [SMILES: CCCCCC(=O)N[C@@H](Cc1ccc(N)cc1)C(=O)N[C@@H](CCCC)C(=O)N[C@@H](CC(C)C)C(=O)[C@@]1(C)CO1] | L-amino-Phe | L-Nle | L-Leu-EK | 5.99 ± 1.08 | 6.32 ± 4.99 | 1.06 |
| 5 | 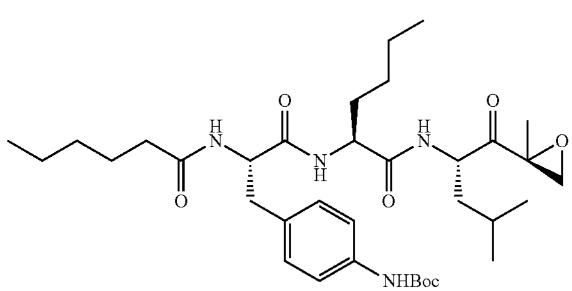 [SMILES: CCCCCC(=O)N[C@@H](Cc1ccc(NC(=O)OC(C)(C)C)cc1)C(=O)N[C@@H](CCCC)C(=O)N[C@@H](CC(C)C)C(=O)[C@@]1(C)CO1] | L-Boc-Phe | L-Nle | L-Leu-EK | 5.55 ± 0.230 | 80.2 ± 26.5 | 14.45 |

TABLE 2-continued illustrates carmaphycin B and analogs 1-20

| Comp # | Structure | P3 | P2 | P1 | P. falciparum Dd2 IC50 [nM] | HepG2 IC50 [nM] | Selectivity Index |
|---|---|---|---|---|---|---|---|
| 6 | 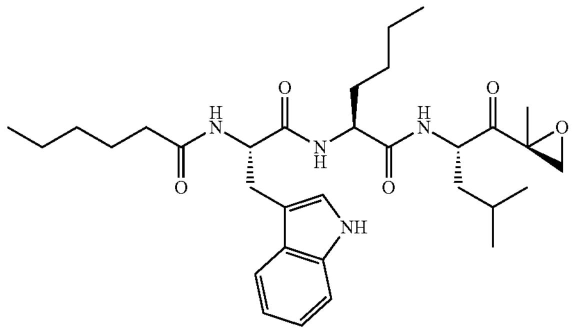 [SMILES: CCCCCC(=O)N[C@@H](Cc1c[nH]c2ccccc12)C(=O)N[C@@H](CCCC)C(=O)N[C@@H](CC(C)C)C(=O)[C@@]1(C)CO1] | L-Trp | L-Nle | L-Leu-EK | 3.11 ± 0.026 | 3.27 ± 1.29 | 1.05 |
| 7 | 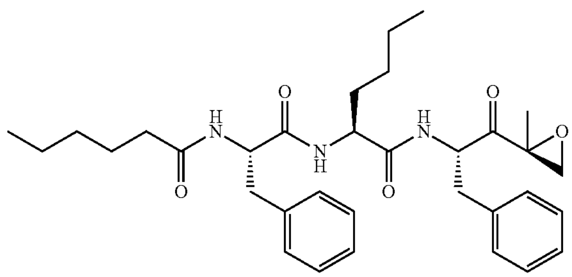 [SMILES: CCCCCC(=O)N[C@@H](Cc1ccccc1)C(=O)N[C@@H](CCCC)C(=O)N[C@@H](Cc1ccccc1)C(=O)[C@@]1(C)CO1] | L-Phe | L-Nle | L-Phe-EK | 6.70 ± 0.451 | 30.8 ± 13.7 | 4.60 |
| 8 | 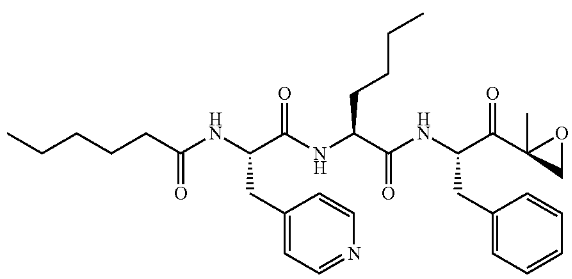 [SMILES: CCCCCC(=O)N[C@@H](Cc1ccncc1)C(=O)N[C@@H](CCCC)C(=O)N[C@@H](Cc1ccccc1)C(=O)[C@@]1(C)CO1] | L-Pyr-Ala | L-Nle | L-Phe-EK | 3.87 ± 1.37 | <0.283 | 0.07 |
| 9 | 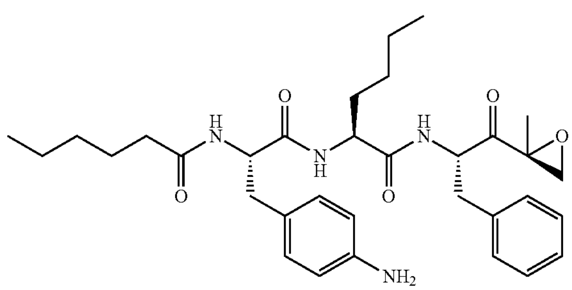 [SMILES: CCCCCC(=O)N[C@@H](Cc1ccc(N)cc1)C(=O)N[C@@H](CCCC)C(=O)N[C@@H](Cc1ccccc1)C(=O)[C@@]1(C)CO1] | L-amino-Phe | L-Nle | L-Phe-EK | 81.8 ± 14.0 | 3410 ± 2310 | 41.69 |
| 10 | 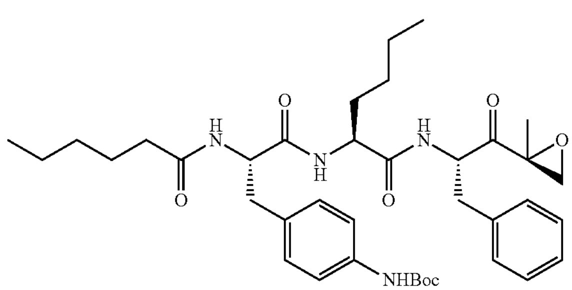 [SMILES: CCCCCC(=O)N[C@@H](Cc1ccc(NC(=O)OC(C)(C)C)cc1)C(=O)N[C@@H](CCCC)C(=O)N[C@@H](Cc1ccccc1)C(=O)[C@@]1(C)CO1] | L-Boc-Phe | L-Nle | L-Phe-EK | 5.45 ± 2.49 | 478 ± 126 | 87.71 |

TABLE 2-continued
illustrates carmaphycin B and analogs 1-20
| Comp # | Structure | P3 | P2 | P1 | P. falciparum Dd2 IC50 [nM] | HepG2 IC50 [nM] | Selectivity Index |
|---|---|---|---|---|---|---|---|
| 11 | 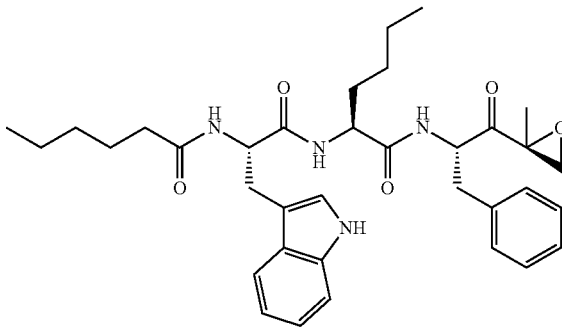 | L-Trp | L-Nle | L-Phe-EK | 9.77 ± 1.31 | 6.41 ± 2.26 | 0.66 |
| 12 | 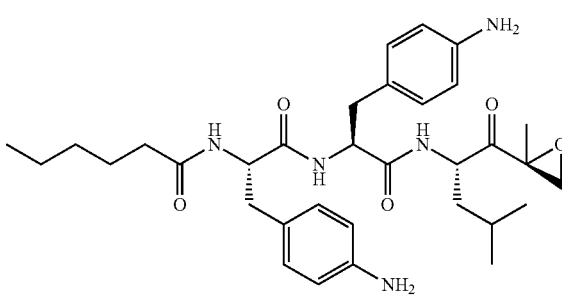 | L-amino-Phe | L-amino-Phe | L-Leu-EK | 59.6 ± 15.4 | 0.91 ± 0.25 | 0.02 |
| 13 | 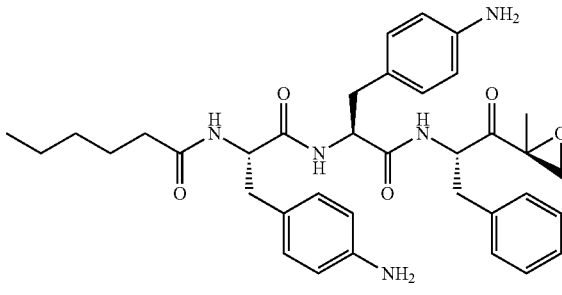 | L-amino-Phe | L-amino-Phe | L-Phe-EK | 68.2 ± 15.4 | 952 ± 275 | 13.96 |
| 14 | 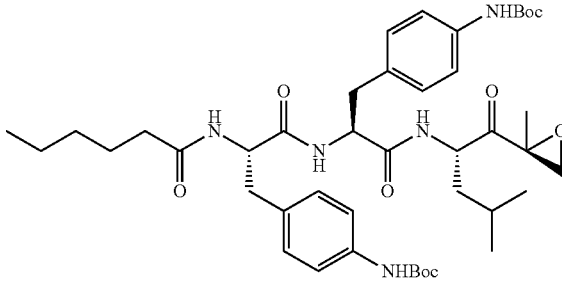 | L-Boc-Phe | L-Boc-Phe | L-Leu-EK | 13.5 ± 4.69 | 118 ± 21.7 | 8.74 |
| 15 | 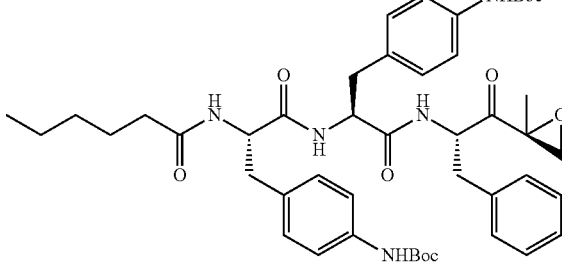 | L-Boc-Phe | L-Boc-Phe | L-Phe-EK | 12.2 ± 3.83 | 45.7 ± 15.7 | 3.75 |

TABLE 2-continued illustrates carmaphycin B and analogs 1-20

| Comp # | Structure | P3 | P2 | P1 | P. falciparum Dd2 IC50 [nM] | HepG2 IC50 [nM] | Selectivity Index |
|---|---|---|---|---|---|---|---|
| 16 | 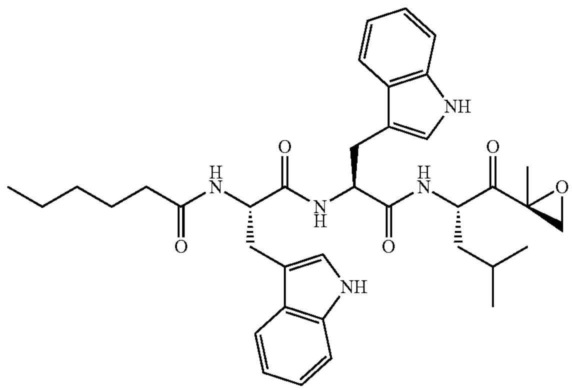 [SMILES: CCCCCC(=O)N[C@@H](Cc1c[nH]c2ccccc12)C(=O)N[C@@H](Cc1c[nH]c2ccccc12)C(=O)N[C@@H](CC(C)C)C(=O)[C@@]1(C)CO1] | L-Trp | L-Trp | L-Leu-EK | 3.70 ± 0.144 | 11.7 ± 3.32 | 3.16 |
| 17 | 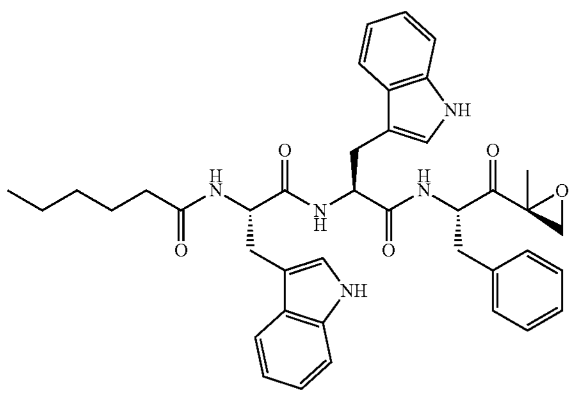 [SMILES: CCCCCC(=O)N[C@@H](Cc1c[nH]c2ccccc12)C(=O)N[C@@H](Cc1c[nH]c2ccccc12)C(=O)N[C@@H](Cc1ccccc1)C(=O)[C@@]1(C)CO1] | L-Trp | L-Trp | L-Phe-EK | 9.38 ± 0.667 | 346 ± 86.2 | 36.89 |
| 18 | O-Val | O-Val | L-Nle | L-Leu-EK | 3.27 ± 0.232 | 1240 ± 274 | 379.20 |
| 19 | O-Trp | O-Trp | L-Nle | L-Leu-EK | 2.92 ± 0.403 | 915 ± 289 | 313.36 |

TABLE 2-continued illustrates carmaphycin B and analogs 1-20

| Comp # | Structure | P3 | P2 | P1 | P. falciparum Dd2 IC50 [nM] | HepG2 IC50 [nM] | Selectivity Index |
|---|---|---|---|---|---|---|---|
| 20 | D-Pyr-Ala (structure shown) | D-Pyr-Ala | L-Nle | L-Leu-EK | 21.8 ± 3.67 | <0.283 | 0.01 |

In Vitro Validation of Carmaphycin B Analogs

Figure 3A:
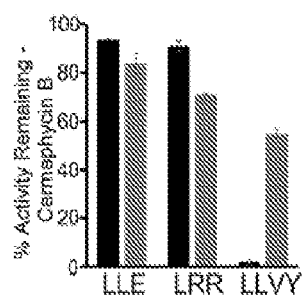
Figure 8A:
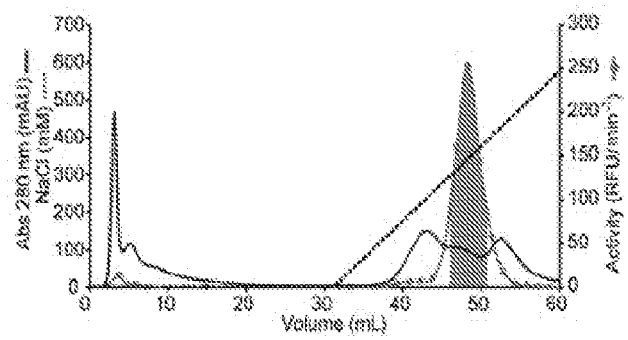
FIGS. 8A-8C shows purification of the proteasome from human, both constitutive and immune, as well as from *P. falciparum* blood stage parasites.
Figure 8B:
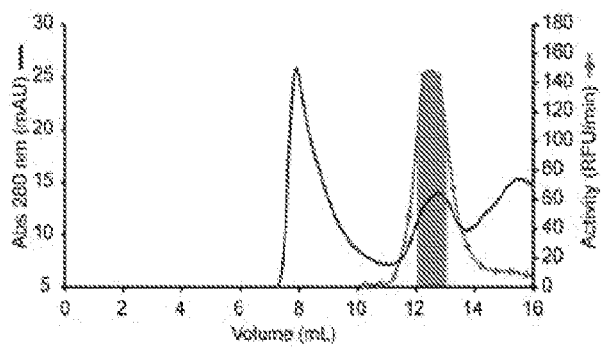
Figure 8C:
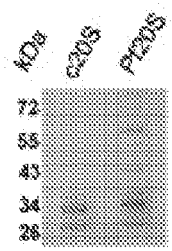

The cell based assays identified carmaphycin B analogs with selectivity indices ranging from 0.02 (analog 12) to 379.20 (analog 18). Therefore, the six compounds with selectivity indices of >30 were further evaluated in biochemical assays. To accomplish this, the 20S *Plasmodium* proteasome (Pf20S) that was enriched from schizont lysate was first isolated using a two-step column chromatography protocol (FIGS. 8A-8C). The concentration of Pf20S proteasome was determined based on subunit protein levels when compared to the human constitutive 20S (c20S) proteasome on a silver stained protein gel (FIG. 8A-8C). Using 0.3 nM of each proteasome, proteolytic activity was then compared using well defined human proteasome substrates, z-LLE-AMC, z-LRR-AMC and suc-LLVY-AMC ("LLVY" disclosed as SEQ ID NO: 1) that are preferentially cleaved by the β1, β2 and β5 subunits, respectively. When c20S was assayed in the presence of 150 nM carmaphycin B, β5 activity was inhibited by 98% while β1 and β2 activity were reduced by 6% and 9% respectively. These data clearly show that carmaphycin B preferentially targets the human β5 subunit. Pf20S hydrolyzed z-LRR-AMC and suc-LLVY-AMC ("LLVY" disclosed as SEQ ID NO: 1) at rates similar to the c20S (within 2-fold) while z-LLE-AMC activity by Pf20S was 19-fold lower than for c20S (FIG. 3A). Addition of 150 nM carmaphycin B resulted in β5 activity being reduced by 45%, while β1 and β2 were reduced by 16% and 29%, respectively. Therefore, carmaphycin B targets all three subunits of the *P. falciparum* proteasome but is a more potent inhibitor of the β5 subunit.

Figure 3B:
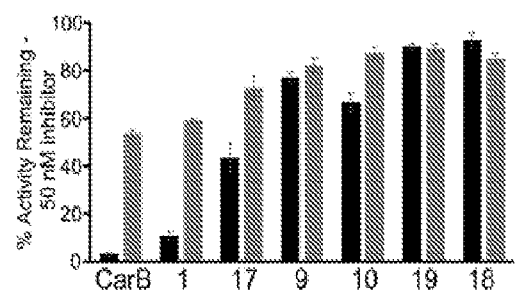
Figure 7:
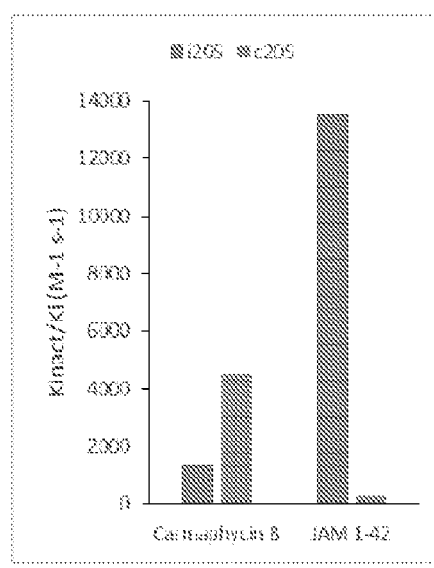
FIG. 7. JAM 1-42 (Analog 18) is 47-fold more selective for i20S when compared to c20S.

Inhibition of the β5 subunit was then evaluated using 50 nM of carmaphycin B and the six *P. falciparum* selective analogs. For the human c20S, β5 activity in the presence of carmaphycin B and 1 was reduced by 97% and 89%, respectively, however analogs 18 and 19 were much less potent and decreased activity by 10% or less (FIG. 3B). At 50 nM concentration, all compounds inhibited Pf20S β5 activity by between 10 and 47% and only analog 18 was more potent towards Pf20S than c20S. These results were further confirmed in whole cell in vitro assays, where treatment of trophozoite-stage parasites with carmaphycin B or the six analogs mentioned above all inhibited *P. falciparum* β5 activity by 40-60% (FIG. 3C). Finally, analog 18 exhibited the same subunit specificity as carmaphycin B, and addition of 450 nM of this compound resulting in a decrease in β5 activity of 45%, while β1 and β2 were reduced by 6% and 9%, respectively. Interestingly, analogs 18 and 1 differ by only the chirality of the P3 valine residue.

Peptide epoxyketone proteasome inhibitors are irreversible and therefore their absolute potency is most accurately described by their inactivation kinetics ($k_{inact}/K_i$). The $k_{inact}/K_i$ for carmaphycin B was calculated to be 4,481 $M^{-1}$ $s^{-1}$ for c20S and 864.3 for Pf20S (Table 3). Substitution of L-methionine sulfone with L-norleucine in P2 in analog 1 results in a 3-fold loss in potency to c20S (1500.3 $M^{-1}$ $s^{-1}$) and no significant change to Pf20S (767.7 $M^{-1}$ $s^{-1}$). However, substitution of the P3 L-valine in 1 with D-valine in 18 resulted in a 100-fold loss in potency to the human c20S proteasome but only a 10-fold reduction to the Pf20S proteasome. These data confirmed that modifications of the P2 and P3 residues of carmaphycin B resulted in the design of a peptide epoxyketone (analog 18) that selectivity inhibits the *Plasmodium* proteasome.

TABLE 3

Calculation of inactivation kinetics for carmaphycin B and analogs 1 and 18.

| | c20S | | | Pf20S | | |
|---|---|---|---|---|---|---|
| Compound | CarB | 1 | 18 | CarB | 1 | 18 |
| $K_{inact}$ ($s^{-1}$) | 1.68 × $10^{-3}$ | 5.62 × $10^{-3}$ | 6.2 × $10^{-4}$ | 1.92 × $10^{-4}$ | 1.76 × $10^{-3}$ | 5.88 × $10^{-5}$ |
| $K_I$ (nM) | 374.9 | 3,744 | 39,213 | 222.6 | 2,294 | 371.7 |
| $K_{inact}/K_I$ ($M^{-1}$ $s^{-1}$) | 4,481 | 1500.3 | 15.8 | 864.3 | 767.7 | 158.1 |

Figures 9A, 9B:
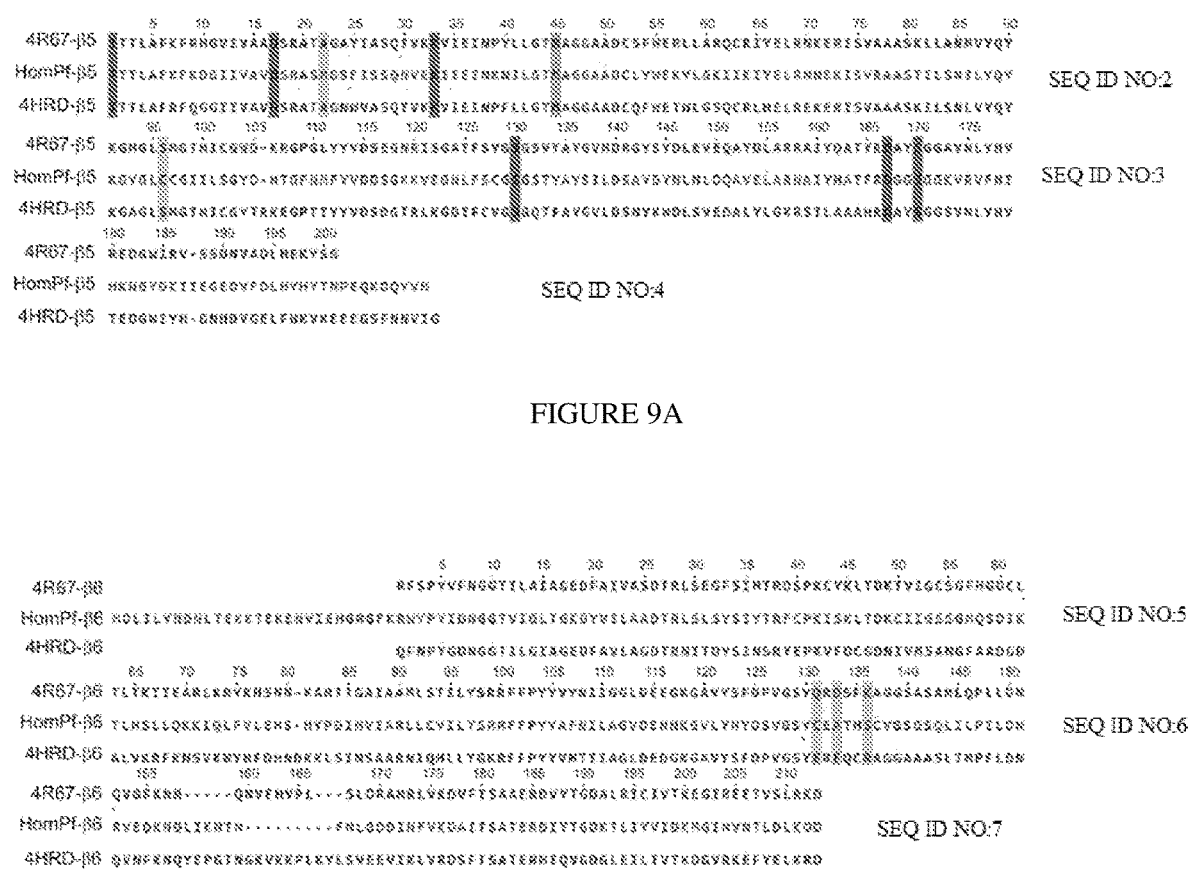

Selectivity Modeling of Carmaphycin B/Analog 18 Towards the Human β5 Binding Pocket and the Model of the Pf β5 Binding Pocket To better understand the molecular basis for the observed specificity of compound 18 towards the *Plasmodium* 20S proteasome β5 subunit, the binding mode of carmaphycin B and 18 towards the human and the parasite proteasome was investigated using molecular modeling approaches. A homology model system of the *plasmodium* 20S proteasome β5 and β6 subunits (homPf_β5) was created based on the crystal structure of the homologous human 20S proteasome (PDB ID 4R67) and the *plasmodium* 20S proteasome cryo-EM structure (PDB ID 5FMG) (27, 28). In addition, sequence alignment of the *Plasmodium* and human β5 and β6 protein chains provided valuable information about modifications that could be responsible for differences in substrate specificity. Using molecular docking experiments in combination with the sequence alignment, key residues that contribute to the binding differences were identified (Table 7, FIGS. 9A-9B).

The binding pose of carmaphycin A to the yeast 20S proteasome β5 subunit was described earlier (FIGS. 2A-2B) and was used as starting point for the analysis (18). In molecular docking experiments, a very similar binding mode of carmaphycin B in the human and *Plasmodium* 20S proteasome β5 subunit was observed (29). In contrast, the molecular docking experiments of compound 18 revealed a switch in the binding position of 18 as a result of the altered stereochemistry of the P3 D-valine residue (FIG. 4A-4D). In this switched position, the P4 fatty acid residue occupies the S3 binding pocket whereas the P3 residue is exposed to the inner cavity of the protein complex. The human S3 pocket is also more restricted in length whereas the parasitic S3 pocket has a longer pore-like structure. This structure of the *plasmodium* S3 pocket is therefore more likely to accommodate the long lipophilic hexanoate residue of compound 18 in the switched position than the human S3 pocket. This switched binding position was previously observed for P3 D-Ala containing compounds binding to the yeast 20S proteasome β5 subunit (26).

Carmaphycin B Synergy with Artemisinin

In *Plasmodium falciparum*, artemisinin (ART) treatment induces growth retardation and accumulation of ubiquitinated proteins, indicating that this family of drugs activates the cell stress response and saturates the ability of the proteasome to degrade these proteins. ART-resistant parasites cope with higher levels of ubiquitinated proteins by increasing substrate turnover using the parasite proteasome. Unsurprisingly, co-treatment of parasites with dihydroartemisinin and clinically approved proteasome inhibitors strongly synergize ART activity against both sensitive and resistant strains (11). Based upon this recognized synergy, this disclosure sought to determine whether carmaphycin B and analog 18 also shared similar synergistic properties. When wild-type parasites were treated with ART, an IC50 of between 19.7 and 23.3 nM was obtained. Co-treatment of wild-type parasites with ART and 0.5 and 1 nM of carmaphycin B resulted in 2-fold and 3-fold sensitization to ART (FIG. 5A). In addition, co-treatment with ART and 0.5 and 1 nM of analog 18 (FIG. 5B) yielded a similar increase in ART sensitivity.

Proteasome inhibitors have shown excellent potential as antimalarial compounds, particularly in light of their tremendous synergy with artemisinin's mechanism of action. This study reports on efforts to design and evaluate proteasome inhibitors based on the carmaphycin B scaffold, and to identify analogs that have potent antimalarial activity with low host cytotoxicity. The lead compound has a 100-fold wider therapeutic window than carmaphycin B and consists of the substitutions of D-valine for L-valine, and norleucine for methionine sulfone. This compound was shown to retain potent antimalarial efficacy in cell-based assays against both asexual blood stages and gametocytes, and strongly inhibits the activity of the isolated *Plasmodium* proteasome in vitro. Moreover, in vitro evolution in *S. cerevisiae*, biochemical assays and molecular modeling studies confirm that this activity is due to specific inhibition of the β5 subunit of the proteasome. Furthermore, molecular modeling of these inhibitors with the β5-subunit of the human versus parasite proteasome determined that subtle structural differences in the β5-subunit active site permit this selectivity.

The rational inhibitor design used in this study was focused on developing compounds with reduced toxicity to human cells. It has been clearly shown that introducing a D-amino acid in the P3 position can significantly alter host cytotoxicity without greatly interfering with anti-*plasmodium* activity. The molecular modeling of this compound with the β5-subunit of the human and parasite proteasome determined that subtle structural differences in the Pf20S β5-subunit active site permit this selectivity and provide the structural basis for the design of more parasite-specific proteasome inhibitors. This insight will prove critical as more inhibitors are developed in the treatment of malaria and other tropical parasitic diseases.

An important characteristic of any anti-malarial compound is that it has oral bioavailability. An oral proteasome inhibitor has been approved for treatment of multiple myeloma that consists of a prodrug that is released under aqueous conditions into a peptide boronic acid proteasome inhibitor. In addition, two orally bioavailable epoxyketone inhibitors have been developed that have potent antimyeloma activity (20805366, 26158521). One of these inhibitors, ONX 0912, is in Phase 1 clinical trial. These anti-cancer drug studies will provide the framework for design of anti-*plasmodium* proteasome inhibitors with good pharmacokinetic and pharmacodynamic properties.

Materials and Methods

*S. cerevisiae* Susceptibility and Dose-Response Assay $ABC_{16}$-Monster yeast cells (15) were inoculated into 5 ml of liquid YPD media and grown to saturation (OD600>1.0) overnight at 200 RPM in a shaking incubator at 30° C. Cultures were diluted to OD600 0.005 to log phase. 100 µl of yeast cells were added to a 96-well plate and incubated with compound starting with a concentration of 150 µM, followed by 1:2 serial dilutions. An initial reading of OD600 (t=0 hrs) was recorded using a Synergy HT spectrophotometer, and cells were grown for a period of 18 hours at 30° C. After incubation, plates were read at OD600. Cells grown in the absence of compound were used as a negative control. Percent growth was calculated using the formula $Ab600_{treated}/Ab600_{control} \times 100$ $IC_{50}$ values were determined by first subtracting the OD600 values at t=0 from those of the final reading and then using Graphpad Prism to calculate nonlinear regression on log(inhibitor) vs. response with variable slope (four parameters).

Selection of Carmaphycin B-Resistant *S. cerevisiae*

Varied concentrations of carmaphycin B were added to 50 ml conical tubes containing 20 µl of saturated $ABC_{16}$-Monster cells in 20 ml of YPD media. Each selection was cultured under vigorous shaking until the culture reached saturation. Saturated cultures were diluted into fresh YPD media containing carmaphycin B, and multiple rounds of selection under increased drug pressure were performed. Cells of ulturescultures that were able to grow in substantially higher drug concentrations than the parental cell line, were streaked onto agar plates containing carmaphycin B to select for monoclonal colonies. Single colonies were isolated, and IC$_{50}$ assays were performed to determine the degree of evolved resistance vs. that of the parental strain.

Whole-Genome Sequencing and Analysis

For whole-genome sequencing (WGS), DNA was extracted from yeast cells using the YeaStar Genomic DNA kit. Genomic yeast DNA libraries were normalized to 0.2 ng/μL and prepared for sequencing according to the manufacturer's instructions using the Illumina Nextera XT kit whole-genome resequencing library (Illumina, Inc., San Diego). DNA libraries were clustered and run on an Illumina HiSeq as 2×100 paired end reads, according to the manufacturer's instructions. Base calls were made using the software CASAVA v1.8.2. Initial sequence alignments were performed using the PLaTyPuS software (30). Reads were aligned to the reference S. cerevisiae genome using BWA, and unmapped reads were filtered using SAMTools. SNVs were called using GATK and filtered using the PLaTyPuS software (30).

Accession Codes

Sequences have been placed in the short read sequence archive (http://www.ncbi.nlm.nih.gov/sra) under accession code SAMN06345855 for lineage 1, SAMN06345856 for lineage 2 and SAMN06345857 for lineage 3.

P. falciparum Culture

P. falciparum Dd2 strain parasites were cultured under standard conditions (31), using RPMI media supplemented with 0.05 mg/ml gentamycin, 0.014 mg/mL hypoxanthine (prepared fresh), 38.4 mM HEPES, 0.2% Sodium Bicarbonate, 3.4 mM Sodium Hydroxide, 0.05% O+ Human Serum (Denatured at 560 C for 40 min and From Interstate Blood Bank, Memphis, Tenn.) and 0.0025% Albumax). Human O+ whole blood was obtained from TSRI blood bank (La Jolla, Calif.). Leukocyte-free erythrocytes are stored at 50% hematocrit in RPMI-1640 screening media (as above, but without O+ human serum and with 2× albumax concentration) at 4° C. for one to three weeks before experimental use. Cultures were monitored every one to two days via Giemsa-stained thin smears.

Compound Sensitivity Assay Using SYBR® Green I

Compound susceptibility was measured using the malaria SYBR Green I-based fluorescence assay (32). Asynchronous P. falciparum parasites (Dd2 strain) were cultured in standard conditions before being plated for the assays. Each compound was tested over 72 hours in technical duplicates on a twelve-point concentration curve prepared by three-fold dilution from 6.7 μM to 0.11 nM. At least three independent experiments were carried out for IC$_{50}$ determination. Artemisinin and chloroquine were used as controls. IC$_{50}$ values were obtained using normalized fluorescence intensity from SYBR green I and analyzed via non-linear variable slope four-parameter regression curve-fitting model in Prism 6 (GraphPad Software Inc).

P. falciparum Induction and Compound Sensitivity Testing of Stage V Gametocytes

Gametocytes were induced in NF54 or derived clones as previously described (33). Asexual blood stage parasites were synchronized at ring stage using 5% sorbitol for three consecutive life cycles. Once the culture reached a parasitemia of 8-10% ring stages, half of the media was exchanged to stress the parasites. Twenty-four hours later, the culture media was exchanged with fresh media and the culture was shaken overnight. The following day, the culture was treated with 50 mM N-acetyl-glucosamine (NAG) (in complete media), and new media containing NAG was added every day for 10 days to clear remaining asexual blood stage parasites and enrich for gametocytes. After 10 days, complete media without NAG was provided each day for the last two days of gametocyte development in order to obtain ~1% gametocytemia with >80% Stage V specificity and no visible asexual blood stage parasites (assessed via Giemsa-stained thin smears). Drug Sensitivity of Stage V gametocytes were then determined using a published protocol using mitotracker red (34). Each compound was tested in technical triplicate in a ten-point concentration curve prepared by three-fold dilution starting at 12.5 μM. At least three independent experiments were carried out for EC$_{50}$ determination and puromycin was used as a positive control. EC$_{50}$ values were obtained using the normalized bioluminescence intensity and a non-linear variable slope four-parameter regression curve-fitting model in Prism 6 (GraphPad Software Inc).

P. berghei-Luciferase Liver Stage Assay and HepG2 Cytotoxicity Assay

The liver-stage and HepG2 toxicity assays were performed as previously reported (35). Briefly, HepG2-A16-CD81EGFP, human hepatocarcinoma HepG2 cells stably transformed to express the tetraspanin CD81 receptor (36, 37) and thus susceptible to P. berghei infection, were cultured at 37° C. in 5% CO2 in DMEM (Life Technologies, Calif.) supplemented with 10% FBS, 0.29 mg/ml glutamine, 100 unit penicillin and 100 μg/ml streptomycin. For both the P. berghei-luciferase and HepG2 cytotoxicity assays, 3×10$^3$ of the HepG2-A16-CD81EGFP cells in 5 μl of assay medium (DMEM without Phenol Red (Life Technologies, Calif.), 5% FBS, and 5× Pen Strep Glutamine (Life Technologies, Calif.)) at concentration 6×10$^5$ cells/ml were seeded in 1536-well plates (Greiner BioOne white solid bottom custom GNF mold) 20-26 hours prior to the actual infection. 18 hours prior to infection, 50 nl of compound in DMSO (0.5% final DMSO concentration per well) were transferred with Acoustic Transfer System (ATS) (Biosero) into the assay plates. Atovaquone (12-point serial dilution starting at 10 μM) and Puromycin (12-point serial dilution starting at 10 μM) were used as positive controls for Pb. liver stage assay and HepG2 cytotoxicity respectively. 0.5% DMSO was used as negative control for the both assays.

An. stephensi mosquitoes, infected with P. berghei-luciferase, were provided by the New York University Insectary. P. berghei-luciferase sporozoites were freshly dissected from the infected A. stephensi mosquito salivary glands, filtered twice through a 20 μm nylon net filter using Steriflip Vacuum-Driven Filtration System (Millipore), counted in a hemocytometer, and then adjusted to final concentration 200 sporozoites per μl in the assay media. For the P.b. liver stage assay, the HepG2-A16-CD81EGFP cells were then infected with 1×10—3 sporozoites per well (5 μl) with a single tip Bottle Valve liquid handler (GNF), and the plates were spun down at 37° C. for 3 minutes in an Eppendorf 5810 R centrifuge at 330 g. The HepG2-A16-CD81EGFP cell designated for toxicity studies were left uninfected, with 5 ul of additional assay media added to each well to maintain equal concentrations of compounds with P. berghei-luciferase infected plates. After incubation at 37° C. for 48 hours the exoerythrocytic growth and HepG2-A16-CD81EGFP cell viability were quantified by a bioluminescence measurement.

In order to assess P. berghei development via bioluminescence, media was removed by spinning the inverted plates at 150×g for 30 seconds. 2 μl BrightGlo (Promega) were being dispensed with the MicroFlo (BioTek) liquid handler. Immediately after addition of the luminescence reagent, the plates were read by the Envision Multilabel Reader (PerkinElmer). IC$_{50}$ values were obtained using the normalized bioluminescence intensity and a non-linear variable slope four-parameter regression curve-fitting model in Prism 6 (GraphPad Software Inc).

The HepG2 cytotoxicity was assessed by removing the media through an inverted spin of the plates at 150 g for 30 s and addition of 2 µL of CellTiterGlo reagent (Promega diluted 1:2 with deionized water) per well using the Micro-Flo liquid handler (BioTek). Immediately after addition of the luminescence reagent, the plates were vortexed for 10 s and read with an EnVision Multilabel reader (PerkinElmer). IC50 values were obtained as above.

Parasite Isolation and Protein Extraction

Asynchronous *P. falciparum* cultures were grown up to 4-5% parasitemia, in 300 mL of RPMI media at 5.0% hematocrit. Cultures were then transferred to 50 mL conical tubes, pelleted via centrifugation at 800 g for 5 min, and washed once with 1×PBS and pelleted again as above. The PBS was removed and lysis buffer (0.15% saponin in PBS) was added on ice in 10 pellet volumes. Upon lysis of red blood cells, indicated by a clear red supernatant, the lysed cultures were centrifuged at 3200×g for 12 minutes at 4° C. The supernatant was removed by aspiration and the cells were washed twice using chilled PBS in microcentrifuge tubes. The cell pellets were then incubated on ice for 1 hour with occasional vortexing in a buffer consisting of 20 mM Tris-HCl pH 7.5, 5 mM MgCl2, 1 mM DTT, 100 µM E-64 and 1 mM AEBSF. This sample was then subjected to 3 rounds of freezing (−80° C.) and thawing (37° C.) and centrifugation at 6000×g for 10 min. The supernatant containing soluble *P. falciparum* protein was quantified by the BCA method (Pierce).

Enrichment of *P. falciparum* Proteasome

*P. falciparum* proteasome was enriched by two-chromatographic steps reported previously (10). In brief, 10 mg of *P. falciparum* protein was concentrated to 1 mL using a 100 kDa centrifugal filter unit (Amicon) and loaded onto a 5 mL anion exchange HiTrap DEAE FF column (GE Healthcare). Protein was eluted using a linear gradient from 0 to 1 M NaCl and 1.5 mL fractions were collected and all fractions were assayed with 25 µM Succinyl-Leu-Leu-Val-Tyr-aminocoumarin (Suc-LLVY-AMC) ("Leu-Leu-Val-Tyr" and "LLVY" disclosed as SEQ ID NO: 1) in assay buffer (20 mM Tris pH 7.5, 0.02% SDS). The AMC fluorophore release was monitored at Ex 340/Em 465 nm at 24° C. using a Synergy HTX multi-mode reader (Biotek). Proteolytically active fractions were pooled and concentrated to 0.5 mL using a 100 kDa centrifugal filter unit (Amicon) and loaded onto a Superose 6 10/300 GL column (GE healthcare). Proteins were eluted using 20 mM Tris-HCl pH 7.5, 100 mM NaCl, 10% glycerol and 1 mL fractions were collected, evaluated for protease activity and pooled.

Proteasome Activity Assays

To estimate the concentration of Pf20S in the final pooled sample, protein was denatured and loaded into a 4-12% Bis-Tris Plus gel (Thermo Fisher Scientific) beside 60 to 100 ng of human constitutive proteasome (Boston Biochem). The gel was silver stained (Thermo Fisher Scientific) and Pf20S subunit concentration was estimated using Image J software. Proteasome activity assays were performed using 0.29 nM of Pf20S or c20S and 25 µM of Suc-LLE-AMC, Suc-LRR-AMC or Suc-LLVY-AMC ("LLVY" disclosed as SEQ ID NO: 1) in assay buffer. For inhibition assays, inhibitor and substrate were added simultaneously to the enzyme and the rate of AMC release was determined from 60 to 120 minutes and compared to a DMSO control. To investigate which proteasome subunits are targeted by Carmaphycin B, assays were performed using 150 nM on inhibitor and the three substrates outlined above, and a similar evaluation was performed with analog 18 at 450 nM Additional inhibition assays were performed using 50 nM of compounds and only Suc-LLVY-AMC ("LLVY" disclosed as SEQ ID NO: 1).

Evaluation of On-Target Proteasome Inhibition

Synchronized early trophozoite parasites were incubated with 95 nM of inhibitors for 4 hr. Parasites were washed and protein lysates were prepared as described above. 15 µg of total protein was combined with 25 µM Suc-LLVY-AMC ("LLVY" disclosed as SEQ ID NO: 1) in assay buffer and activity was evaluated as outlined above. Inhibition of proteasome activity was compared to DMSO treated cells.

Calculation of Inhibition Constants

To calculate inhibition constants, activity assays were performed as described above except using 200 µM Suc-LLVY-AMC substrate ("LLVY" disclosed as SEQ ID NO: 1). The rate of AMC release was calculated in the presence of serial dilution of each inhibitor. The rate of product formation were calculated at 30 min intervals for 4 hours, and normalized to activity DMSO control to calculate inactivation curves. $K_{obs}$ values for each inhibitor concentration were calculated from inactivation curves, and inhibition constants $K_I$ and $k_{inact}$ were calculated by non-linear regression of $K_{obs}$ and inhibitor concentration using GraphPad Prism 6 software.

Molecular Modeling

Molecular Operating Environment (MOE) 2016.08 (Chemical Computing Group, Montreal, QC, Canada) was used to perform the molecular modeling experiments and to create all pictures. The Amber10:EHT force field as implemented in MOE was used for all energy minimization calculations. All covalent docking experiments were performed using the Docktite application (38). The pharmacophore method with London dG scoring was used for placement of the ligands and refined with the induced fit method with GBVI/WSA dG rescoring. The docking application was adapted to the binding of a seven-membered ring system instead of a 6-membered ring system to comply with the most recent literature (29).

Mutant modeling: The yeast proteasomal crystal structure in complex with carmaphycin A (PDB ID 4HRD) was used as a template for mutation modeling analysis. PDB ID 4HRD chain K complies with proteasome component PRE2 (PRE2 sequence position 76-287=PDB residue 1-212). The M45 residue was mutated with the Protein Builder and the resulting model was energy minimized. The β5 and β6 subunit together with crystal water molecules in a radius of 4.5 Å from receptor or ligand were used for further analysis.

Homology model: The homology model system of the *plasmodium* 20S proteasome β5 and β6 subunits (homPf_b5) was created based on the crystal structure of the homologous human 20S proteasome (PDB ID 4R67) and the sequence information of the *plasmodium* 20S proteasome cryo-EM structure (PDB ID 5FMG). The human 20S proteasome was used as template and the individual subunits were aligned to construct several models of the Pf 20S proteasome. The models were scored using the GB/VI scoring method and the final model was protonated with Prononate3D and energy minimized to an RMS gradient of 0.5. The geometry of the homology model was examined.

Analog Synthesis

In order to obtain the 20 analogs described in this study, a convergent, flexible and scalable synthesis procedure was used that avoids racemization, a common problem in the synthesis of peptide-like structures. The synthesis of these analogues was divided into two parts, the leucine-EK part (P1) and the dipeptide part which contains the P2-P3-P4 moieties, and each of these two parts was synthesized separately according to a previously established procedure. The synthesis was completed by attaching the Leu-EK moiety (P1) to the desired dipeptide moiety (P2-P3-P4) using simple HBTU/HOBt coupling to afford the desired analogues. In case of Boc-protected compounds 4, 10, 12 and 14, the protecting group was cleaved by TFA/DCM and the crude compound was purified on RP-HPLC to afford their free amine analogues 5, 9, 13, 15.

A solution of intermediate (0.2 mmol, 1 equiv.) and LiOH.H$_2$O (2.0 mmol, 10 equiv.) in 1,4-dioxane/H$_2$O (20 mL, 2:1) was stirred at 25° C. After 1.5 h, all volatiles were evaporated off and the resulting residue was suspended in H$_2$O (10 mL), acidified and extracted with EtOAc (3×10 mL). The combined organic extracts were dried using anhydrous sodium sulfate and concentrated to obtain the free acid of the intermediate as a white solid. In a separate reaction, Boc-L-epoxyketone derivatives (0.7 mmol) in CH$_2$Cl$_2$ (5 mL) was treated with TFA (1 mL, 13.0 mmol) and stirred at 25° C. for 1 h, whereupon it was concentrated in vacuo to a reddish oil. A fraction of this oil (0.14 mmol, 1.2 equiv) was dissolved in CH$_2$Cl$_2$ (2 mL) and added to a solution of the previously prepared free acid (0.12 mmol, 1.0 equiv) and HBTU (0.14 mmol, 1.2 equiv) in CH$_2$Cl$_2$ (10 mL) at 25° C.; followed by addition of DiPEA (0.264 mmol, 2.2 equiv). After stirring for 3-5 h at 25° C., the reaction mixture was quenched with saturated NH$_4$Cl, followed by solvent partition and CH$_2$Cl$_2$ (3×15 mL) extractions of the aqueous layer. All organic extracts were combined and dried using anhydrous sodium sulfate, and concentrated in vacuo. Silica gel column chromatography (10-100% EtOAc/hexanes) yielded pure compounds 1-20.

A Jasco P-2000 polarimeter was used to measure optical rotations. NMR spectra were recorded on a Bruker 500 MHz spectrometer (500 and 125 MHz for the $^1$H and $^{13}$C nuclei, respectively) using CDCl$_3$ or CD$_3$OD as solvent from Cambridge Isotope Laboratories, Inc. (99.8% D). Spectra were referenced to residual CDCl$_3$ solvent as internal standard ($\delta_H$ 7.26 and $\delta_C$ 77.1). LC-HRMS data for analysis of compounds 1-20 were obtained on an Agilent 6239 HR-ESI-TOFMS equipped with a Phenomenex Luna 5 μm C18 100 Å column (4.6×250 mm). Semi-preparative HPLC purification was carried out using a Waters 515 with a Waters 996 photodiode array detector using Empower Pro software. All solvents were HPLC grade.

Supplemental Tables

TABLE 4

Table 4: Carmaphycin B resistant strains

|  | GM | Lineage 1 | Lineage 2 | Lineage 3 |
|---|---|---|---|---|
| average IC50 (uM) | 24.2775 | >150 | 52.7325 | >100 |
| SEM (n = 4) | 0.295 |  | 2.66 |  |

TABLE 5

Table 5: Sequencing Statistics for *S. cerevisiae* resistant clones

|  | Lineage 1 (R7c-2) | Lineage 2 (R8b-2) | Lineage 3 (R9b-2) |
|---|---|---|---|
| Total reads | 30,725,372 | 32,374,374 | 25,823,710 |
| Aligned reads | 30,176,825 | 31,915,743 | 25,391,150 |
| Percent Aligned Reads | 98.2147 | 98.5834 | 98.325 |
| Mean Coverage | 210.95 | 221.46 | 179.16 |
| Percent bases covered by 5 or more reads | 99.4 | 99.4 | 99.4 |
| Mean read length | 100 | 100 | 100 |
| Median insert size | 218 | 224 | 231 |

TABLE 6

Table 6. Results of whole-genome sequencing of the three resistant lines. Mutations in genes encoding ubiquitination or proteasomal proteins are bolded.

| Lineage | Chr | Position | Codon Change | Gene Mutated | Gene Name | AA Change | Functional Class |
|---|---|---|---|---|---|---|---|
| Lineage 1 | II | 473356 | Gcg/Tcg | YBR115C | LYS2 | A191S | Missense |
|  | III | 1142221 | Gtc/Ctc | YDR335W | MSN5 | V352L | Missense |
|  | VII | 943119 | gGg/gCg | YGR224W | AZR1 | G105A | Missense |
|  | VII | 386978 | Cgt/Ggt | YGL062W | PYC1 | R595G | Missense |
|  | VII | 261789 | agC/agG | YGL131C | SNT2 | S1357R | Missense |
|  | XV | 177382 | Att/Gtt | YOL081W | IRA2 | I2105V | Missense |
|  | XV | 100169 | Agg/Tgg | YOL116W | MSN1 | R121W | Missense |
|  | XV | 656199 | Gaa/Aaa | YOR172W | YRM1 | E664K | Missense |
|  | VI | 70366 | caT/caC | YFL033C | RIM15 | H1354 | Silent |
| Lineage 2 | V | 229448 | Gtg/Atg | YER039C |  | V12M | Missense |
|  | XV | 539008 | cTt/cCt | YOR115C | TRS33 | L153P | Missense |
|  | XVI | 732708 | atG/atT | YPR103W | PRE2 | M120I | Missense |
|  | XIII | 380730 | ctC/ctG | YMR053C | STB2 | L723 | Silent |
| Lineage 3 | IV | 310485 |  |  |  |  | Intergenic |
|  | IV | 126219 | Gtc/Ctc | YDL186W |  | V202L | Missense |
|  | V | 469834 | gCg/gAg | YER151C | UBP3 | A864E | Missense |
|  | V | 562119 | ttG/ttT | YER186C |  | L169F | Missense |
|  | VII | 742995 | gCc/gTc | YGR125W |  | A224V | Missense |
|  | VIII | 68009 | Gac/Cac | YHL019C | APM2 | D514H | Missense |
|  | XI | 102346 | cCa/cGa | YKL182W | FAS1 | P559R | Missense |
|  | XI | 84734 | Gac/Cac | YKL189W | HYM1 | D11H | Missense |
|  | XII | 447263 | Ccc/Gcc | YLR153C | ACS2 | P105A | Missense |
|  | XIII | 319043 | Agt/Cgt | YMR022W | UBC7 | S122R | Missense |

TABLE 6-continued

Table 6. Results of whole-genome sequencing of the three resistant lines. Mutations in genes encoding ubiquitination or proteasomal proteins are bolded.

| Lineage | Chr | Position | Codon Change | Gene Mutated | Gene Name | AA Change | Functional Class |
|---|---|---|---|---|---|---|---|
| | XIV | 550739 | Gat/Cat | YNL041C | COG6 | D417H | Missense |
| | XIV | 326862 | aCa/aGa | YNL163C | RIA1 | T1071R | Missense |
| | XV | 656188 | aAc/aTc | YOR172W | YRM1 | N660I | Missense |
| | XII | 627141 | tcG/tcA | YLR246W | ERF2 | S8 | Silent |
| | XVI | 702831 | aaA/aaG | YPR081C | GRS2 | K380 | Silent |

TABLE 7

Table 7: Amino acid residues in the β5 binding pocket in the human 20S proteasome (PDB ID 4R67) and equivalent residue substitutions in the plasmodial 20S proteasome (PDB ID 5FMG) that were identified to be associated with the preferred binding of analog 18 towards the plasmodium 20S proteasome β5 subunit.

| Protein chain | Position* | Human 20S Proteasome | P. falciparum 20S Proteasome |
|---|---|---|---|
| β5 | 22 | Ala | Met |
| | 96 | Ser | Cys |
| β6 | 131 | Gln | Cys |
| | 133 | Asp | Ala |
| | 136 | Lys | Ser |

Validation Data for Carmaphycin B Analogs

Analog 1

Analog 1: (S)-2-((S)-2-hexanamido-3-methylbutanamido)-N—((S)-4-methyl-1-((R)-2-methyloxiran-2-yl)-1-oxopentan-2-yl)hexanamide. Smile: O═C(N[C@@H](C(C)C)C(N[C@@H](CCCC)C(N[C@@H](CC(C)C)C([C@]1(CO1)C)═O)═O)═O)CCCCC Yield 42%; [α]$^{28}_D$ +23 (c 0.8, CHCl$_3$); $^1$H NMR (500 MHz, CDCl$_3$) δ 6.73 (m, 2H), 6.35 (t, J=6.9 Hz, 1H), 4.54 (ddd, J=10.9, 8.0, 3.2 Hz, 1H), 4.40 (q, J=7.5 Hz, 1H), 4.25 (t, J=8.1 Hz, 1H), 3.24 (d, J=5.0 Hz, 1H), 2.84 (d, J=5.0 Hz, 1H), 2.26-2.10 (m, 2H), 1.96 (q, J=6.9 Hz, 1H), 1.73-1.68 (m, 1H), 1.62-1.53 (m, 3H), 1.52-1.47 (m, 1H), 1.45 (d, J=3.1 Hz, 3H), 1.29-1.13 (m, 10H), 0.87-0.76 (m, 18H). $^{13}$C NMR (126 MHz, CDCl$_3$) δ 208.6, 173.3, 171.5, 171.3, 59.0, 58.2, 52.9, 52.4, 50.1, 39.9, 36.6, 31.9, 31.4, 31.2, 27.4, 25.4, 25.1, 23.3, 22.3, 21.1, 19.1, 18.3, 16.7, 13.9, 13.8. HRESIMS m/z [M+Na]$^+$ 481.3519 (calcd for C26H47N3O5, 481.3516).

Analog 2

Analog 2: (S)-2-((S)-2-hexanamido-3-phenylpropanamido)-N—((S)-4-methyl-1-((R)-2-methyloxiran-2-yl)-1-oxopentan-2-yl)hexanamide. Smile: O═C(N[C@@H](CC1═CC═CC═C1)C(N[C@@H](CCCC)C(N[C@@H](CC(C)C)C([C@]2(CO2)C)═O)═O)═O)CCCCC Yield 52%; [α]$^{28}_D$ −4 (c 0.6, CHCl$_3$); $^1$H NMR (500 MHz, CDCl$_3$) δ 7.27-7.23 (m, 2H), 7.23-7.20 (m, 1H), 7.20-7.14 (m, 2H), 6.95 (d, J=7.6 Hz, 1H), 6.63 (d, J=7.8 Hz, 1H), 6.53 (d, J=8.0 Hz, 1H), 6.20 (d, J=7.7 Hz, 1H), 4.74 (q, J=6.9 Hz, 0H), 4.58 (ddd, J=10.9, 7.9, 3.1 Hz, 0H), 4.37 (q, J=7.1 Hz, 0H), 3.31 (d, J=5.0 Hz, 1H), 3.06 (q, J=6.7, 6.0 Hz, 1H), 2.89 (dd, J=5.2, 1.6 Hz, 0H), 2.15 (t, J=7.6 Hz, 2H), 1.71-1.78 (m, 2H), 1.66-1.68 (m, 1H), 1.52 (s, 3H), 1.50-1.58 (m, 4H), 1.22-1.32 (m, 4H), 1.15-1.22 (m, 4H), 0.93-0.97 (m, 6H), 0.85 (t, J=7.3 Hz, 3H), 0.84 (t, J=7.4 Hz, 3H). $^{13}$C NMR (125 MHz, CDCl$_3$) δ 208.6, 173.6, 171.7, 171.4, 136.3, 129.2, 128.6, 126.9, 59.2, 53.9, 53.2, 52.5, 50.7, 50.4, 39.7, 38.0, 36.4, 31.9, 31.3, 27.4, 25.3, 25.2, 23.4, 22.3, 22.3, 21.2, 16.8, 13.9, 13.9. HRESIMS m/z [M+Na]$^+$ 552.3406 (calcd for C$_{30}$H$_{47}$N$_3$O$_5$Na, 552.3413).

Analog 3

Analog 3: (S)-2-((S)-2-hexanamido-3-(pyridin-4-yl)propanamido)-N—((S)-4-methyl-1-((R)-2-methyloxiran-2-yl)-1-oxopentan-2-yl)hexanamide. Smile: O═C(N[C@@H](CC1═CC═NC═C1)C(N[C@@H](CCCC)C(N[C@@H](CC(C)C)C([C@]2(CO2)C)═O)═O)═O)CCCCC Yield 62%; [α]$^{28}_D$ +6 (c 0.2, CHCl$_3$); $^1$H NMR (500 MHz, CDCl$_3$) δ 8.51 (d, J=4.6 Hz, 2H), 7.13 (d, J=4.6 Hz, 2H), 6.70 (d, J=7.8 Hz, 1H), 6.24 (d, J=8.0 Hz, 1H), 6.06 (d, J=7.9 Hz, 1H), 4.91-4.73 (m, 1H), 4.67-4.53 (m, 1H), 4.31 (td, J=7.7, 5.8 Hz, 1H), 3.29 (d, J=5.0 Hz, 1H), 3.15 (dd, J=14.1, 6.5 Hz, 1H), 3.00 (dd, J=14.1, 7.3 Hz, 1H), 2.92 (d, J=5.1 Hz, 1H), 2.16 (t, J=7.5 Hz, 2H), 1.78 (dq, J=13.6, 6.6, 6.1 Hz, 1H), 1.63-1.54 (m, 4H), 1.53 (s, 1H), 1.35-1.17 (m, 8H), 0.97 (t, J=6.3 Hz, 3H), 0.96 (t, J=6.6 Hz, 3H), 0.88 (m, 6H). $^{13}$C NMR (126 MHz, CDCl$_3$) δ 208.4, 173.4, 171.1, 170.2, 149.9, 145.4, 124.5, 59.1, 53.3, 52.9, 52.4, 50.4, 39.9, 37.0, 36.4, 32.1, 31.2, 27.4, 25.2, 25.2, 23.3, 22.3, 22.3, 21.2, 16.7, 13.9, 13.8. HRESIMS m/z [M+Na]$^+$ 553.3367 (calcd for C$_{29}$H$_{46}$N$_4$O$_5$Na, 553.3366).

Analog 4

Analog 4: (S)-2-((S)-3-(4-aminophenyl)-2-hexanamidopropanamido)-N—((S)-4-methyl-1-((R)-2-methyloxiran-2-yl)-1-oxopentan-2-yl)hexanamide. Smile: O═C(N[C@@H](CC1═CC═C(N)C═C1)C(N[C@@H](CCCC)C(N[C@@H](CC(C)C)C([C@]2(CO2)C)═O)═O)═O)CCCCC Yield 50%; [α]$^{28}_D$ +19 (c 1.0, CHCl$_3$); $^1$H NMR (500 MHz, CDCl$_3$) δ 6.90 (d, J=7.8 Hz, 2H), 6.53 (d, J=7.9 Hz, 2H), 6.36 (d, J=7.8 Hz, 1H), 6.32 (d, J=7.9 Hz, 1H), 5.93 (d, J=7.3 Hz, 1H), 4.59-4.41 (m, 2H), 4.25 (td, J=7.7, 5.7 Hz, 1H), 3.25 (d, J=5.0 Hz, 1H), 2.89 (h, J=7.0 Hz, 2H), 2.83 (d, J=5.0 Hz, 1H), 2.08 (t, J=7.6 Hz, 2H), 1.76-1.65 (m, 1H), 1.58 (ddt, J=13.4, 6.7, 4.1 Hz, 1H), 1.50-1.45 (m, 2H), 1.47 (s, 3H), 1.28-1.08 (m, 11H), 0.89 (m, 6H), 0.80 (m, 6H). $^{13}$C NMR (126 MHz, CDCl$_3$) δ 208.3, 173.4, 171.3, 171.1, 145.3, 130.0, 125.8, 115.3, 59.1, 54.3, 53.2, 52.4, 50.3, 39.8, 36.9, 36.50, 31.8, 31.3, 27.3, 25.2, 23.4, 22.3, 22.3, 21.3, 16.7, 13.9, 13.9. HRESIMS m/z [M+Na]$^+$ 567.3520 (calcd for C$_{30}$H$_{48}$N$_4$O$_5$Na, 567.3522).

Analog 5

Analog 5: tert-butyl (4-((S)-2-hexanamido-3-(((S)-1-(((S)-4-methyl-1-((R)-2-methyloxiran-2-yl)-1-oxopentan-2-yl)amino)-1-oxohexan-2-yl)amino)-3-oxopropyl)phenyl)carbamate. Smile: O═C(N[C@@H](CC1═CC═C(NC(OC(C)(C)C)═O)C═C1)C(N[C@@H](CCCC)C(N[C@@H](CC(C)C)([C@]2(CO2)C)═O)═O)═O)CCCCC Yield 81%; [α]$^{28}_D$ −38 (c 0.6, CHCl$_3$); $^1$H NMR (500 MHz, CDCl$_3$) δ 7.33-7.24 (m, 2H), 7.15-7.06 (m, 2H), 6.65 (d, J=7.7 Hz, 1H), 6.54-6.47 (m, 2H), 6.13 (d, J=7.5 Hz, 1H), 4.67 (q, J=7.0 Hz, 1H), 4.57 (tt, J=10.5, 2.7 Hz, 1H), 3.32 (d, J=5.0 Hz, 1H), 3.01 (m, 1H), 2.94-2.89 (m, 1H), 2.15 (td, J=7.7, 2.1 Hz, 2H), 1.75 (m, 4H), 1.68-1.62 (m, 1H), 1.59-1.49 (m, 2H), 1.51 (s, 9H), 1.34-1.15 (m, 6H), 0.95 (dt, J=5.6, 2.6 Hz, 6H), 0.86 (td, J=7.2, 2.1 Hz, 6H). $^{13}$C NMR (126 MHz, CDCl$_3$) δ 208.4, 173.5, 171.3, 171.0, 152.6, 137.3, 130.6, 129.7, 118.6, 80.5, 59.1, 54.1, 53.2, 52.4, 50.3, 39.8, 37.1, 36.4, 31.9, 31.3, 28.3, 27.3, 25.2, 23.3, 22.3, 22.3, 21.2, 16.7, 13.9, 13.9. HRESIMS m/z [M+Na]$^+$ 667.4050 (calcd for C$_{35}$H$_{56}$N$_4$O$_7$Na, 667.4047).

Analog 6

Analog 6: (S)-2-((S)-2-hexanamido-3-(1H-indol-3-yl)propanamido)-N—((S)-4-methyl-1-((R)-2-methyloxiran-2-yl)-1-oxopentan-2-yl)hexanamide. Smile: O=C(N[C@@H](CC1=CNC2=C1C=CC=C2)C(N[C@@H](CCCC)C(N[C@@H](CC(C) C)C([C@]3(CO3)C)=O)=O)=O)CCCCC Yield 48%; [α]$^{28}_D$ +23 (c 1.6, CHCl$_3$); $^1$H NMR (500 MHz, CDCl$_3$) δ 8.27 (s, 1H), 7.71 (d, J=7.9 Hz, 1H), 7.37 (d, J=8.1 Hz, 1H), 7.21 (t, J=7.5 Hz, 1H), 7.14 (t, J=7.3 Hz, 1H), 7.09 (s, 1H), 6.42 (d, J=7.9 Hz, 1H), 6.40 (d, J=7.8 Hz, 1H), 6.27 (d, J=7.3 Hz, 1H), 4.77 (q, J=7.0 Hz, 1H), 4.56 (ddd, J=10.9, 8.0, 3.3 Hz, 1H), 4.30 (td, J=7.7, 5.5 Hz, 1H), 3.32 (td, J=14.7, 5.4 Hz, 2H), 3.17 (dd, J=14.7, 7.4 Hz, 1H), 2.90 (t, J=4.7 Hz, 1H), 2.16 (t, J=7.6 Hz, 2H), 1.71-1.78 (m, 2H), 1.65-1.69 (m, 1H), 1.52 (s, 3H), 1.46-1.58 (m, 4H), 1.19-1.35 (m, 4H), 1.15-1.22 (m, 4H), 0.90-0.98 (m, 6H), 0.85 (t, J=7.3 Hz, 3H), 0.84 (t, J=7.4 Hz, 3H). $^{13}$C NMR (126 MHz, CDCl$_3$) δ 208.6, 173.5, 171.5, 171.4, 136.2, 127.4, 123.2, 122.4, 119.9, 118.7, 111.3, 110.4, 59.1, 53.7, 53.4, 52.5, 50.2, 40.4, 39.8, 36.6, 31.7, 31.4, 27.9, 27.3, 25.2, 23.4, 23.4, 22.4, 22.3, 21.3, 16.8, 13.9, 13.9. HRESIMS m/z [M+Na]$^+$ 591.3518 (calcd for C$_{32}$H$_{48}$N$_4$O$_5$Na, 591.3522).

Analog 7

Analog 7: (S)-2-((S)-2-hexanamido-3-phenylpropanamido)-N—((S)-1-((R)-2-methyloxiran-2-yl)-1-oxo-3-phenylpropan-2-yl)hexanamide. Smile: O=C(N[C@@H](CC1=CC=CC=C1)C(N[C@@H](CCCC)C(N[C@@H](CC2=CC=CC=C2)C([C@]3(CO3)C)=O)=O)=O)CCCCC Yield 28%; [α]$^{28}_D$ −68 (c 0.5, CHCl$_3$); $^1$H NMR (500 MHz, CDCl$_3$) δ 7.29 (dd, J=14.8, 7.4 Hz, 2H), 7.26-7.20 (m, 2H), 7.19-7.15 (m, 2H), 7.14-7.10 (m, 2H), 6.67 (d, J=6.8 Hz, 1H), 6.53 (t, J=6.3 Hz, 1H), 6.20 (d, J=6.4 Hz, 1H), 4.80 (td, J=7.8, 4.9 Hz, 1H), 4.67 (q, J=7.2 Hz, 1H), 4.30 (q, J=7.1 Hz, 1H), 3.33 (d, J=4.9 Hz, 1H), 3.12 (dd, J=13.9, 5.0 Hz, 1H), 2.99 (tt, J=13.9, 7.3 Hz, 2H), 2.91 (d, J=4.9 Hz, 1H), 2.79 (dd, J=13.9, 8.2 Hz, 1H), 2.15 (t, J=7.6 Hz, 2H), 1.81 (m, 2H), 1.67 (ddt, J=16.1, 9.3, 4.3 Hz, 1H), 1.55 (td, J=7.5, 5.1 Hz, 1H), 1.49 (s, 3H), 1.1-1.3 (m, 8H), 0.85 (t, J=7.3 Hz, 3H), 0.84 (t, J=7.4 Hz, 3H). $^{13}$C NMR (125 MHz, CDCl$_3$) δ 207.6, 173.4, 171.0, 170.8, 136.4, 135.7, 129.3, 129.2, 128.7, 128.6, 127.2, 127.0, 59.3, 54.1, 53.1, 52.7, 52.5, 37.9, 37.1, 36.5, 31.8, 31.3, 27.3, 25.3, 22.4, 22.3, 16.5, 13.9, 13.9. HRESIMS m/z [M+Na]$^+$ 586.3265 (calcd for C$_{33}$H$_{45}$N$_3$O$_5$Na, 586.3257).

Analog 8

Analog 8: (S)-2-((S)-2-hexanamido-3-(pyridin-4-yl)propanamido)-N—(S)-1-((R)-2-methyloxiran-2-yl)-1-oxo-3-phenylpropan-2-yl)hexanamide. Smile: O=C(N[C@@H](CC1=CC=NC=C1)C(N[C@@H](CCCC)C(N[C@@H](CC2=CC=CC=C2)C([C@]3 (C3)C)=O)=O)=O)CCCCC Yield 48%; [α]$^{28}_D$ −24 (c 1.0, CHCl$_3$); $^1$H NMR (500 MHz, CDCl$_3$) δ 8.42-8.36 (d, J=4.5 Hz, 2H), 7.25 (m, 3H), 7.13-7.06 (m, 2H), 6.98 (d, J=4.5 Hz, 2H), 6.46 (d, J=7.7 Hz, 1H), 6.29 (d, J=7.4 Hz, 1H), 5.92 (d, J=7.9 Hz, 1H), 4.72 (td, J=7.6, 4.2 Hz, 1H), 4.60 (q, J=7.3 Hz, 1H), 4.15 (td, J=7.7, 5.7 Hz, 1H), 3.24 (d, J=4.9 Hz, 1H), 3.09 (dd, J=14.1, 4.9 Hz, 1H), 2.95 (dd, J=14.1, 6.7 Hz, 1H), 2.89 (d, J=7.3 Hz, 1H), 2.87 (d, J=4.9 Hz, 1H), 2.71 (dd, J=14.1, 8.1 Hz, 1H), 2.07 (t, J=7.6 Hz, 2H), 1.61-1.57 (m, 2H), 1.50-1.45 (m, 4H), 1.44 (s, 3H), 1.28-1.06 (m, 8H), 0.80 (t, J=7.1 Hz, 3H), 0.78 (t, J=7.4 Hz, 3H). $^{13}$C NMR (126 MHz, CDCl$_3$) δ 207.3, 173.4, 170.8, 170.2, 149.9, 145.4, 135.5, 129.3, 128.7, 127.2, 124.4, 59.3, 53.2, 53.0, 52.8, 52.6, 37.0, 36.9, 36.4, 31.8, 31.2, 27.2, 25.2, 22.3, 22.3, 16.6, 13.9, 13.8. HRESIMS m/z [M+Na]$^+$ 587.3211 (calcd for C$_{32}$H$_{44}$N$_4$O$_5$Na, 587.3209).

Analog 9

Analog 9: (S)-2-((S)-3-(4-aminophenyl)-2-hexanamidopropanamido)-N—((S)-1-((R)-2-methyloxiran-2-yl)-1-oxo-3-phenylpropan-2-yl)hexanamide. Smile: O=C(N[C@@H](CC1=CC=C(N)C=C1)C(N[C@@H](CCCC)C(N[C@@H](CC2=CC=C C=C2)C([C@]3(CO3)C)=O)=O)=O)CCCCC Yield 31%; [α]$^{28}_D$ +22 (c 0.9, CHCl$_3$); $^1$H NMR (500 MHz, CDCl$_3$) δ 7.28-7.21 (m, 3H), 7.11-7.08 (m, 2H), 6.85 (d, J=8.1 Hz, 2H), 6.50 (d, J=8.1 Hz, 2H), 6.30 (d, J=7.5 Hz, 1H), 6.10 (d, J=7.5 Hz, 1H), 5.87 (d, J=7.3 Hz, 1H), 4.70 (td, J=8.0, 4.9 Hz, 1H), 4.43 (q, J=7.0 Hz, 1H), 4.20-4.08 (m, 1H), 3.27 (d, J=5.0 Hz, 1H), 3.06 (dd, J=14.0, 4.9 Hz, 1H), 2.92-2.83 (m, 2H), 2.72 (ddd, J=25.3, 14.0, 7.8 Hz, 2H), 2.08 (t, J=7.6 Hz, 2H), 1.62-1.47 (m, 3H), 1.43 (s, 3H), 1.40-1.29 (m, 1H), 1.19 (ddt, J=19.4, 12.9, 5.8 Hz, 6H), 1.03 (q, J=7.5 Hz, 2H), 0.84-0.79 (m, 3H), 0.76 (t, J=7.3 Hz, 3H). $^{13}$C NMR (125 MHz, CDCl$_3$) δ 207.5, 173.4, 171.0, 170.9, 136.3, 135.7, 129.3, 129.2, 128.7, 128.6, 127.2, 127.3, 115.6, 59.3, 54.1, 53.1, 52.7, 52.5, 37.9, 37.1, 36.5, 31.8, 31.3, 27.3, 25.3, 22.4, 22.3, 16.6, 13.9, 13.9. HRESIMS m/z [M+Na]$^+$ 601.3375 (calcd for C$_{33}$H$_{46}$N$_4$O$_5$Na, 601.3366).

Analog 11

Analog 11: (S)-2-((S)-2-hexanamido-3-(1H-indol-3-yl)propanamido)-N—((S)-1-((R)-2-methyloxiran-2-yl)-1-oxo-3-phenylpropan-2-yl)hexanamide. Smile: O=C(N[C@@H](CC1=CNC2=C1C=CC=C2)C(N[C@@H](CCCC)C(N[C@@H](CC3=CC=CC=C3)C([C@]4(CO4)C)=O)=O)=O)CCCCC Yield 69% [α]$^{28}_D$ +54 (c 0.9, CHCl$_3$); $^1$H NMR (500 MHz, CDCl$_3$) δ 8.09 (d, J=2.3 Hz, 1H), 7.72 (d, J=7.9 Hz, 1H), 7.37-7.29 (m, 4H), 7.19 (dt, J=8.3, 1.3 Hz, 1H), 7.17-7.08 (m, 4H), 6.88 (d, J=2.5 Hz, 1H), 6.43 (d, J=7.6 Hz, 1H), 6.31 (d, J=7.3 Hz, 1H), 6.12 (d, J=7.8 Hz, 1H), 4.74 (m, 2H), 4.23 (td, J=7.7, 5.6 Hz, 1H), 3.33 (t, J=5.5 Hz, 1H), 3.27 (dd, J=14.5, 5.5 Hz, 1H), 3.19-3.01 (m, 2H), 2.95-2.89 (m, 1H), 2.72-2.63 (m, 1H), 2.23-2.13 (m, 2H), 1.76 (m, 2H), 1.65-1.57 (m, 2H), 1.51 (s, 3H), 1.37-1.22 (m, 4H), 1.19-1.12 (m, 2H), 1.05-0.95 (m, 2H), 0.87 (td, J=7.1, 1.4 Hz, 3H), 0.78 (td, J=7.4, 1.4 Hz, 3H). $^{13}$C NMR (126 MHz, CDCl$_3$) δ 207.7, 173.4, 171.4, 171.0, 136.1, 135.9, 135.5, 129.3, 128.6, 127.1, 123.2, 122.4, 119.8, 118.8, 111.3, 110.3, 59.3, 53.7, 53.1, 52.7, 52.6, 37.1, 36.9, 36.5, 31.6, 31.3, 28.1, 27.1, 25.2, 22.3, 22.2, 16.5, 13.9, 13.8. HRESIMS m/z [M+H]$^+$ 603.3549 (calcd for C35H46N4O5H, 603.3546).

Analog 12

Analog 12: N—((R)-3-(4-aminophenyl)-1-(((S)-3-(4-aminophenyl)-1-(((S)-4-methyl-1-((R)-2-methyloxiran-2-yl)-1-oxopentan-2-yl)amino)-1-oxopropan-2-yl)amino)-1-oxopropan-2-yl)hexanamide Smile: O=C(N[C@@H](CC1=CC=C(N)C=C1)C(N[C@@H](CC2=CC=C(N)C=C2)C(N[C@@H](CC(C)C)C([C@]3(CO3)C)=O)=O)=O)CCCCC Yield 29%; [α]$^{28}_D$ −16 (c 1.0, CHCl$_3$); $^1$H NMR (500 MHz, CDCl3) δ 6.89 (d, J=8.3 Hz, 2H), 6.78 (d, J=8.4 Hz, 2H), 6.54 (d, J=8.4 Hz, 2H), 6.48 (d, J=8.4 Hz, 2H), 6.16 (d, J=7.8 Hz, 2H), 5.77 (d, J=6.8 Hz, 1H), 4.52-4.33 (m, 3H), 3.23 (dd, J=5.0, 0.7 Hz, 1H), 2.91 (m, 2H), 2.87-2.79 (m, 2H), 2.70 (dd, J=14.0, 6.8 Hz, 1H), 2.00 (t, J=7.7 Hz, 2H), 1.47-1.37 (m, 3H), 1.44 (s, 3H), 1.26-1.11 (m, 6H), 0.87-0.85 (m, 3H), 0.84-0.82 (m, 2H), 0.80 (d, J=7.3 Hz, 3H). HRESIMS m/z [M+Na]$^+$ 616.3470 (calcd for $C_{33}H_{47}N_5O_5Na$, 616.3475).

Analog 13

Analog 13: N—((R)-3-(4-aminophenyl)-1-(((S)-3-(4-aminophenyl)-1-(((S)-1-((R)-2-methyloxiran-2-yl)-1-oxo-3-phenylpropan-2-yl)amino)-1-oxopropan-2-yl)amino)-1-oxopropan-2-yl)hexanamide. Smile: O=C(N[C@@H](CC1=CC=C(N)C=C1)C(N[C@@H](CC2=CC=C(N)C=C2)C(N[C@@H](CC3=CC=CC=C3)C([C@]4(CO4)C)=O)=O)=O)CCCCC Yield 19%; [α]$^{28}$$_D$ +23 (c 1.2, CHCl$_3$); $^1$H NMR (500 MHz, CDCl3) δ 7.19-7.14 (m, 4H), 7.01-6.98 (m, 1H), 6.83 (d, J=8.2 Hz, 1H), 6.78-6.75 (m, 1H), 6.52-6.45 (m, 2H), 6.22 (dd, J=10.4, 7.4 Hz, 1H), 5.88 (d, J=7.1 Hz, 1H), 4.64 (td, J=7.8, 5.0 Hz, 1H), 4.40 (q, J=6.9 Hz, 1H), 4.31 (q, J=7.0 Hz, 1H), 3.23 (d, J=4.9 Hz, 1H), 3.05 (m, 1H), 2.91-2.80 (m, 2H), 2.76 (ddd, J=14.1, 10.3, 6.7 Hz, 1H), 2.67 (dd, J=14.1, 7.0 Hz, 1H), 2.59 (dd, J=14.0, 8.5 Hz, 1H), 2.02 (t, J=7.6 Hz, 2H), 1.57-1.28 (m, 7H), 1.28-1.10 (m, 4H), 0.81 (t, J=7.1 Hz, 6H). $^{13}$C NMR (126 MHz, CD$_3$OD) δ 207.1, 174.8, 172.1, 171.6, 161.8, 136.6, 129.6, 129.4, 128.9, 128.0, 115.4, 58.6, 54.7, 52.6, 51.5, 42.3, 36.8, 36.1, 35.4, 30.9, 25.1, 22.0, 22.0, 17.2, 15.8, 15.2, 12.9, 11.7. HRESIMS m/z [M+Na]$^+$ 650.3317 (calcd for $C_{36}H_{45}N_5O_5Na$, 650.3318).

Analog 14

Analog 14: tert-butyl (4-((R)-3-(((S)-3-(4-((tert-butoxycarbonyl)amino)phenyl)-1-(((S)-4-methyl-1-((R)-2-methyloxiran-2-yl)-1-oxopentan-2-yl)amino)-1-oxopropan-2-yl)amino)-2-hexanamido-3-oxopropyl)phenyl)carbamate. Smile: O=C(N[C@@H](CC1=CC=C(NC(OC(C)(C)C)=O)C=C1)C(N[C@@H](CC2=CC=C(NC (OC(C)(C)C)=O)C=C2)C(N[C@@H](CC(C)C)C([C@]3(CO3)C)=O)=O)=O)CCCCC Yield 42%; [α]$^{28}$$_D$ +35 (c 0.9, CHCl$_3$); $^1$H NMR (500 MHz, CDCl3) δ 7.27 (d, J=8.1 Hz, 2H), 7.22 (d, J=8.1 Hz, 2H), 7.04 (d, J=8.2 Hz, 2H), 6.96 (d, J=8.2 Hz, 2H), 6.71 (s, 1H), 6.67 (s, 1H), 6.57-6.44 (m, 2H), 6.02 (dd, J=7.5, 3.2 Hz, 1H), 4.63-4.57 (m, 2H), 4.53 (td, J=8.0, 4.0 Hz, 1H), 3.26 (d, J=5.0 Hz, 1H), 2.96 (dd, J=13.6, 6.6 Hz, 2H), 2.95-2.93 (m, 2H) 2.89 (d, J=4.8 Hz, 1H), 2.09 (t, J=7.7 Hz, 2H), 1.87 (m, 2H), 1.58-1.48 (m, 18H), 1.26 (td, J=8.0, 7.5, 2.4 Hz, 4H), 1.22-1.16 (m, 2H), 0.92 (d, J=6.1 Hz, 3H), 0.91-0.87 (m, 3H), 0.86 (d, J=7.3 Hz, 3H). $^{13}$C NMR (126 MHz, CDCl3) δ 208.1, 173.7, 170.9, 170.4, 152.8, 137.4, 137.2, 130.6, 130.5, 129.7, 129.6, 118.9, 118.8, 80.5, 59.0, 54.2, 54.1, 52.4, 50.1, 39.8, 37.0, 36.7, 36.3, 31.3, 28.3, 28.3, 25.1, 25.0, 23.3, 22.3, 21.2, 21.1, 16.6, 13.9. HRESIMS m/z [M+Na]$^+$ 816.4526 (calcd for $C_{43}H_{63}N_5O_9Na$, 816.4523).

Analog 15

Analog 15: tert-butyl (4-((R)-3-(((S)-3-(4-((tert-butoxycarbonyl)amino)phenyl)-1-(((S)-1-((R)-2-methyloxiran-2-yl)-1-oxo-3-phenylpropan-2-yl)amino)-1-oxopropan-2-yl)amino)-2-hexanamido-3-oxopropyl)phenyl)carbamate. Smile: O=C(N[C@@H](CC1=CC=C(NC(OC(C)(C)C)=O)C=C1)C(N[C@@H](CC2=CC=C(NC (OC(C)(C)C)=O)C=C2)C(N[C@@H](CC3=CC=CC=C3)C([C@]4(CO4)C)=O)=O)=O)C CCCC Yield 63%; [α]$^{28}$$_D$ −2 (c 1.4, CHCl$_3$); $^1$H NMR (500 MHz, CDCl3) δ 7.27-7.22 (m, 3H), 7.20 (d, J=8.4 Hz, 2H), 7.11-7.05 (m, 2H), 7.03-6.97 (m, 2H), 6.92 (dd, J=8.9, 2.2 Hz, 2H), 6.64 (d, J=13.8 Hz, 2H), 6.45-6.38 (m, 2H), 5.98 (d, J=7.5 Hz, 1H), 4.73 (td, J=8.0, 5.0 Hz, 1H), 4.56 (q, J=7.0 Hz, 1H), 4.48 (q, J=7.2 Hz, 1H), 3.27 (d, J=4.9 Hz, 1H), 3.06 (dd, J=14.0, 5.0 Hz, 1H), 2.99 (dd, J=14.1, 6.6 Hz, 1H), 2.92-2.83 (m, 4H), 2.69 (dd, J=13.9, 8.3 Hz, 1H), 2.10 (td, J=7.6, 1.2 Hz, 2H), 1.54-1.46 (m, 2H), 1.52 (s, 18H), 1.46 (s, 3H), 1.30-1.25 (m, 2H), 1.24-1.16 (m, 2H), 0.87 (t, J=7.2 Hz, 3H). $^{13}$C NMR (126 MHz, CDCl3) δ 207.1, 173.5, 170.8, 170.1, 152.7, 137.3, 137.2, 135.7, 130.6, 129.7, 129.6, 129.3, 128.5, 127.0, 118.8, 80.5, 59.2, 54.1, 54.0, 52.6, 52.5, 37.1, 36.9, 36.8, 36.4, 31.3, 28.3, 28.3, 25.2, 22.3, 16.4, 13.9. HRESIMS m/z [M+Na]$^+$ 850.4368 (calcd for $C_{46}H_{61}N_5O_9Na$, 850.4367).

Analog 16

Analog 16: N—((S)-1-(((S)-3-(1H-indol-3-yl)-1-(((S)-4-methyl-1-((R)-2-methyloxiran-2-yl)-1-oxopentan-2-yl)amino)-1-oxopropan-2-yl)amino)-3-(1H-indol-3-yl)-1-oxopropan-2-yl)hexanamide. Smile: O=C(N[C@@H](CC1=CNC2=C1C=CC=C2)C(N[C@@H](CC3=CNC4=C3C=CC=C4) C(N[C@@H](CC(C)C)C([C@]5(CO5)C)=O)=O)=O)CCCCC Yield 62%; [α]$^{28}$$_D$ +63 (c 0.9, CHCl$_3$); $^1$H NMR (500 MHz, CDCl$_3$) δ 8.40 (s, 1H), 8.14 (s, 1H), 7.69 (d, J=7.9 Hz, 1H), 7.45 (d, J=8.1 Hz, 1H), 7.33-7.25 (m, 3H), 7.21 (t, J=7.6 Hz, 1H), 7.11-7.03 (m, 2H), 6.87 (d, J=2.4 Hz, 1H), 6.69 (dd, J=8.2, 4.4 Hz, 1H), 6.54 (t, J=7.6 Hz, 1H), 6.43 (d, J=8.0 Hz, 1H), 6.26 (d, J=8.1 Hz, 1H), 5.83 (d, J=6.6 Hz, 1H), 4.69 (ddd, J=8.4, 6.2, 4.2 Hz, 1H), 4.61 (t, J=5.9 Hz, 1H), 4.47 (ddd, J=11.1, 8.2, 3.2 Hz, 1H), 3.54-3.48 (m, 1H), 3.29 (dd, J=13.3, 4.5 Hz, 2H), 3.12 (dd, J=14.8, 6.6 Hz, 1H), 2.85 (d, J=4.9 Hz, 1H), 2.77 (dd, J=14.6, 6.2 Hz, 1H), 1.73 (m, 2H), 1.59 (td, J=12.2, 9.1, 4.3 Hz, 1H), 1.48 (s, 3H), 1.45-1.33 (m, 1H), 1.32-1.14 (m, 4H), 1.12-1.00 (m, 3H), 0.89-0.81 (m, 6H), 0.77 (d, J=6.3 Hz, 3H). $^{13}$C NMR (126 MHz, CDCl$_3$) δ 207.9, 173.6, 170.8, 170.7, 136.3, 135.9, 127.5, 127.2, 123.7, 123.3, 122.7, 122.1, 120.2, 119.4, 118.6, 118.1, 111.6, 111.3, 110.1, 109.3, 59.1, 54.2, 53.6, 52.3, 50.1, 39.3, 38.6, 35.7, 31.2, 26.9, 26.6, 24.7, 23.2, 22.3, 21.1, 16.7, 13.9. HRESIMS m/z [M+Na]$^+$ 664.3471 (calcd for $C_{37}H_{47}N_5O_5Na$, 664.3475).

Analog 17

Analog 17: N—((S)-1-(((S)-3-(1H-indol-3-yl)-1-(((S)-1-((R)-2-methyloxiran-2-yl)-1-oxo-3-phenylpropan-2-yl)amino)-1-oxopropan-2-yl)amino)-3-(1H-indol-3-yl)-1-oxopropan-2-yl)hexanamide. Smile: O=C(N[C@@H](CC1=CNC2=C1C=CC=C2)C(N[C@@H](CC3=CNC4=C3C=CC=C4) C(N[C@@H](CC5=CC=CC=C5)C([C@]6(CO6)C)=O)=O)=O)CCCCC Yield 46%; [α]$^{28}$$_D$ +35 (c 0.9, CHCl$_3$); $^1$H NMR (500 MHz, CDCl$_3$) δ 8.29 (s, 1H), 7.85-7.81 (m, 1H), 7.67 (d, J=7.9 Hz, 1H), 7.43 (d, J=8.1 Hz, 1H), 7.30-7.19 (m, 5H), 7.16 (t, J=7.5 Hz, 1H), 7.08 (t, J=7.6 Hz, 1H), 6.99-6.93 (m, 3H), 6.79 (d, J=7.4 Hz, 1H), 6.64 (t, J=7.6 Hz, 1H), 6.50 (d, J=2.7 Hz, 1H), 6.44 (d, J=7.7 Hz, 1H), 6.11 (d, J=7.8 Hz, 1H), 5.90 (d, J=6.7 Hz, 1H), 4.71 (td, J=8.4, 4.4 Hz, 1H), 4.60 (dtd, J=14.3, 6.9, 4.5 Hz, 2H), 3.44 (dd, J=14.8, 4.6 Hz, 1H), 3.29 (d, J=4.9 Hz, 1H), 3.15 (dd, J=14.5, 4.4 Hz, 1H), 3.06 (dd, J=14.7, 7.0 Hz, 1H), 2.96 (dd, J=14.0, 4.4 Hz, 1H), 2.86 (d, J=4.9 Hz, 1H), 2.71 (dd, J=14.6, 6.6 Hz, 1H), 2.54 (dd, J=14.0, 8.9 Hz, 1H), 1.80 (m, 2H), 1.66-1.52 (m, 2H), 1.46 (s, 3H), 1.25 (dt, J=15.3, 7.4 Hz, 2H), 1.19-1.07 (m, 2H), 0.88 (t, J=7.3 Hz, 3H). $^{13}$C NMR (126 MHz, CDCl$_3$) δ 207.1, 173.6, 170.9, 170.7, 136.5, 136.3, 135.7, 129.3, 128.3, 127.4, 127.1, 126.6, 123.7, 123.3, 122.6, 122.0, 120.0, 119.4, 118.7, 118.1, 111.5, 111.2, 110.1, 108.9, 59.2, 54.1, 53.7, 52.7, 52.4, 36.5, 35.8, 31.2, 27.3, 26.6, 24.9, 22.3, 16.5, 14.0. HRESIMS m/z [M+Na]$^+$ 698.3322 (calcd for $C_{40}H_{45}N_5O_5Na$, 698.3318).

Analog 18

Analog 18: (S)-2-((R)-2-hexanamido-3-methylbutanamido)-N—((S)-4-methyl-1-((R)-2-methyloxiran-2-yl)-1-oxopentan-2-yl)hexanamide. Smile: O=C(CCCCC)N[C@H](C(C)C)C(N[C@@H](CCCC)C(N[C@@H](CC(C)C)C([C@]1(C)OC1)=O)=O)=O.

Yield 43%; [α]$^{28}_D$ +54 (c 0.9, CHCl$_3$); $^1$H NMR (500 MHz, Chloroform-d) δ 6.84 (dd, J=7.9, 2.7 Hz, 1H), 6.78 (dd, J=8.3, 2.6 Hz, 1H), 6.39 (dd, J=8.2, 2.6 Hz, 1H), 4.54 (ddd, J=10.8, 7.6, 3.2 Hz, 1H), 4.48-4.39 (m, 1H), 4.22 (td, J=8.0, 2.6 Hz, 1H), 3.32 (dd, J=5.3, 2.5 Hz, 1H), 2.87 (dd, J=5.2, 2.6 Hz, 1H), 2.23 (tt, J=7.8, 2.6 Hz, 2H), 2.08 (qd, J=7.0, 2.6 Hz, 1H), 2.05-2.00 (m, 2H), 1.87-1.77 (m, 1H), 1.72-1.55 (m, 4H), 1.53-1.46 (m, 3H), 1.37-1.19 (m, 6H), 0.93 (ddt, J=9.8, 6.3, 3.1 Hz, 12H), 0.87 (tq, J=6.3, 3.3, 2.7 Hz, 6H). $^{13}$C NMR (150 MHz, CDCl$_3$) δ 209.2, 173.6, 171.5, 171.4, 59.0, 58.8, 52.8, 52.4, 49.9, 39.7, 36.4, 32.1, 31.4, 31.1, 27.5, 25.4, 25.1, 23.3, 22.3, 22.3, 21.1, 19.1, 18.5, 16.6, 13.9, 13.8. HRESIMS m/z [M+Na]$^+$ 504.3404 (calcd for C$_{26}$H$_{47}$N$_3$O$_5$Na, 504.3408).

Analog 19

Analog 19: (S)-2-((R)-2-hexanamido-3-(1H-indol-3-yl)propanamido)-N—((S)-4-methyl-1-((R)-2-methyloxiran-2-yl)-1-oxopentan-2-yl)hexanamide. Smile: O=C(N[C@H](CC1=CNC2=C1C=CC=C2)C(N[C@@H](CCCC)C(N[C@@H](CC(C)C) C([C@]3(CO3)C)=O)=O)=O)CCCCC Yield 42%; [α]$^{28}_D$ +7 (c 0.2, CHCl$_3$); $^1$H NMR (500 MHz, CDCl$_3$) δ 8.15 (s, 1H), 7.67 (d, J=7.9 Hz, 1H), 7.37 (d, J=8.1 Hz, 1H), 7.21 (ddd, J=8.2, 7.1, 1.2 Hz, 1H), 7.15 (ddd, J=8.0, 7.1, 1.1 Hz, 1H), 7.07 (d, J=2.4 Hz, 1H), 6.56 (d, J=7.9 Hz, 1H), 6.24 (d, J=7.1 Hz, 1H), 6.09 (d, J=8.0 Hz, 1H), 4.67 (ddd, J=8.7, 7.1, 6.0 Hz, 1H), 4.51 (ddd, J=10.8, 7.9, 3.2 Hz, 1H), 4.18 (td, J=8.0, 5.6 Hz, 1H), 3.35-3.30 (m, 1H), 3.29-3.24 (m, 1H), 3.18 (dd, J=14.3, 8.7 Hz, 1H), 2.87 (d, J=5.0 Hz, 1H), 2.26-2.10 (m, 2H), 1.66-1.63 (m, 1H), 1.62-1.54 (m, 2H), 1.53-1.46 (m, 4H), 1.35-1.21 (m, 6H), 1.15 (qd, J=7.5, 1.9 Hz, 2H), 0.92 (t, J=6.8 Hz, 6H), 0.87 (t, J=7.1 Hz, 3H), 0.80 (t, J=7.3 Hz, 3H). $^{13}$C NMR (126 MHz, CDCl3) δ 208.3, 173.8, 171.4, 171.4, 136.1, 127.2, 122.9, 122.4, 119.9, 118.6, 111.3, 110.4, 59.1, 54.4, 53.3, 52.4, 50.2, 39.6, 36.4, 31.3, 31.1, 27.9, 27.1, 25.1, 25.1, 23.3, 22.3, 22.2, 21.2, 16.7, 13.9, 13.8. HRESIMS m/z [M+Na]$^+$ 591.3519 (calcd for C$_{32}$H$_{48}$N$_4$O$_5$Na, 591.3522).

Analog 20

Analog 20: tert-butyl (4-((S)-2-hexanamido-3-(((S)-1-(((S)-1-((R)-2-methyloxiran-2-yl)-1-oxo-3-phenylpropan-2-yl)amino)-1-oxohexan-2-yl)amino)-3-oxopropyl)phenyl)carbamate. Smile: O=C(N[C@@H](CC1=CC=C(NC(OC(C)(C)C)=O)C=C1)C(N[C@@H](CCCC)C(N[C@@H](CC2=CC=CC=C2)C([C@]3(CO3)C)=O)=O)=O)CCCCC Yield 72%; [α]$^{28}_D$ +2 (c 0.9, CHCl$_3$); $^1$H NMR (500 MHz, CDCl$_3$) δ 7.29 (m, 3H), 7.23 (t, J=7.2 Hz, 2H), 7.18 (d, J=7.5 Hz, 2H), 7.03 (d, J=8.0 Hz, 2H), 6.68 (d, J=7.3 Hz, 1H), 6.54 (d, J=7.9 Hz, 1H), 6.51 (s, 1H), 6.21 (d, J=7.5 Hz, 1H), 4.79 (td, J=7.8, 4.9 Hz, 1H), 4.61 (q, J=7.2 Hz, 1H), 4.30 (q, J=7.1 Hz, 1H), 3.71 (d, J=8.7 Hz, 1H), 3.33 (d, J=5.0 Hz, 1H), 3.11 (dd, J=13.9, 4.9 Hz, 1H), 2.99-2.85 (m, 3H), 2.77 (dd, J=14.0, 8.3 Hz, 1H), 2.15 (t, J=7.6 Hz, 2H), 1.83 (m, 2H), 1.66 (dt, J=12.0, 5.5 Hz, 1H), 1.55 (td, J=7.8, 5.4 Hz, 2H), 1.51 (s, 9H), 1.49 (s, 3H), 1.45 (m, 1H), 1.24 (dtd, J=18.8, 14.4, 7.1 Hz, 6H), 1.11 (q, J=7.8 Hz, 2H), 0.86 (t, J=7.2 Hz, 3H), 0.82 (t, J=7.3 Hz, 3H). $^{13}$C NMR (126 MHz, CDCl$_3$) δ 207.6, 173.4, 171.0, 152.6, 137.3, 135.8, 130.6, 129.7, 128.6, 127.1, 118.5, 80.5, 59.3, 54.1, 53.1, 52.7, 52.5, 37.2, 37.0, 36.4, 31.8, 31.3, 28.3, 27.2, 25.3, 22.3, 22.3, 16.5, 13.9, 13.8. HRESIMS m/z [M+Na]$^+$ 701.3896 (calcd for C$_{38}$H$_{54}$N$_4$O$_7$Na, 701.3890).

REFERENCES

1. Organization WH (2017) World Malaria Report: 2016.
2. Dondorp A M, et al. (2009) Artemisinin resistance in *Plasmodium falciparum* malaria. *N Engl J Med* 361(5): 455-467.
3. Ariey F, et al. (2014) A molecular marker of artemisinin-resistant *Plasmodium falciparum* malaria. *Nature* 505 (7481):50-55.
4. Hovlid M L & Winzeler E A (2016) Phenotypic Screens in Antimalarial Drug Discovery. *Trends in parasitology* 32(9):697-707.
5. Love M S, et al. (2017) A high-throughput phenotypic screen identifies clofazimine as a potential treatment for cryptosporidiosis. *PLoS Negl Trop Dis* 11(2):e0005373.
6. Kato N, et al. (2016) Diversity-oriented synthesis yields novel multistage antimalarial inhibitors. *Nature* 538 (7625):344-349.
7. Newman D J & Cragg G M (2016) Natural Products as Sources of New Drugs from 1981 to 2014. *Journal of natural products* 79(3):629-661.
8. Wells T N (2011) Natural products as starting points for future anti-malarial therapies: going back to our roots? *Malaria journal* 10 Suppl 1:S3.
9. Pereira A R, et al. (2012) The carmaphycins: new proteasome inhibitors exhibiting an alpha,beta-epoxyketone warhead from a marine cyanobacterium. *Chembiochem: a European journal of chemical biology* 13(6):810-817.
10. Li H, et al. (2012) Validation of the proteasome as a therapeutic target in *Plasmodium* using an epoxyketone inhibitor with parasite-specific toxicity. *Chemistry & biology* 19(12):1535-1545.
11. Dogovski C, et al. (2015) Targeting the cell stress response of *Plasmodium falciparum* to overcome artemisinin resistance. *PLoS Biol* 13(4):e1002132.
12. Infante J R, et al. (2016) A first-in-human dose-escalation study of the oral proteasome inhibitor oprozomib in patients with advanced solid tumors. *Investigational new drugs* 34(2):216-224.
13. Ottilie S, et al. (2017) Rapid Chagas Disease Drug Target Discovery Using Directed Evolution in Drug-Sensitive Yeast. *ACS chemical biology* 12(2):422-434.
14. Goldgof G M, et al. (2016) Comparative chemical genomics reveal that the spiroindolone antimalarial KAE609 (Cipargamin) is a P-type ATPase inhibitor. *Sci Rep* 6:27806.
15. Suzuki Y, et al. (2011) Knocking out multigene redundancies via cycles of sexual assortment and fluorescence selection. *Nature methods* 8(2):159-164.
16. Franke N E, et al. (2012) Impaired bortezomib binding to mutant beta5 subunit of the proteasome is the underlying basis for bortezomib resistance in leukemia cells. *Leukemia* 26(4):757-768.
17. Finley D, Ulrich H D, Sommer T, & Kaiser P (2012) The ubiquitin-proteasome system of *Saccharomyces cerevisiae*. *Genetics* 192(2):319-360.
18. Trivella D B, et al. (2014) Enzyme inhibition by hydroamination: design and mechanism of a hybrid carmaphycin-syringolin enone proteasome inhibitor. *Chemistry & biology* 21(6):782-791.
19. Huber E M, Heinemeyer W, & Groll M (2015) Bortezomib-resistant mutant proteasomes: structural and biochemical evaluation with carfilzomib and ONX 0914. *Structure* (London, England: 1993) 23(2):407-417.

20. Aboulaila M, et al. (2012) Apicoplast-targeting antibacterials inhibit the growth of *Babesia* parasites. *Antimicrobial agents and chemotherapy* 56(6):3196-3206.
21. Kreidenweiss A, Kremsner P G, & Mordmuller B (2008) Comprehensive study of proteasome inhibitors against *Plasmodium falciparum* laboratory strains and field isolates from Gabon. *Malaria journal* 7:187.
22. Czesny B, Goshu S, Cook J L, & Williamson K C (2009) The proteasome inhibitor epoxomicin has potent *Plasmodium falciparum* gametocytocidal activity. *Antimicrobial agents and chemotherapy* 53(10):4080-4085.
23. Bibo-Verdugo B, Jiang Z, Caffrey C R, & O'Donoghue A J (2017) Targeting proteasomes in infectious organisms to combat disease. *The FEBS journal*.
24. Li H, et al. (2016) Structure- and function-based design of *Plasmodium*-selective proteasome inhibitors. *Nature* 530(7589):233-236.
25. Bromme D, Klaus J L, Okamoto K, Rasnick D, & Palmer J T (1996) Peptidyl vinyl sulphones: a new class of potent and selective cysteine protease inhibitors: S2P2 specificity of human cathepsin 02 in comparison with cathepsins S and L. *The Biochemical journal* 315 (Pt 1):85-89.
26. de Bruin G, et al. (2014) Structure-based design of betali or beta5i specific inhibitors of human immunoproteasomes. *J Med Chem* 57(14):6197-6209.
27. Harshbarger W, Miller C, Diedrich C, & Sacchettini J (2015) Crystal structure of the human 20S proteasome in complex with carfilzomib. *Structure* (London, England: 1993) 23(2):418-424.
28. Li H, Bogyo M, & da Fonseca P C (2016) The cryo-EM structure of the *Plasmodium falciparum* 20S proteasome and its use in the fight against malaria. *The FEBS journal* 283(23):4238-4243.
29. Schrader J, et al. (2016) The inhibition mechanism of human 20S proteasomes enables next-generation inhibitor design. *Science* 353(6299):594-598.
30. Manary M J, et al. (2014) Identification of pathogen genomic variants through an integrated pipeline. *Bmc Bioinformatics* 15.
31. Trager W & Jensen J B (1979) Human malaria parasites in continuous culture. *Science* 193:673-675.
32. Johnson J D, et al. (2007) Assessment and continued validation of the malaria SYBR green I-based fluorescence assay for use in malaria drug screening. *Antimicrobial agents and chemotherapy* 51(6):1926-1933.
33. Fivelman Q L, et al. (2007) Improved synchronous production of *Plasmodium falciparum* gametocytes in vitro. *Molecular and Biochemical Parasitology* 154(1):119-123.
34. Plouffe David M, et al. (High-Throughput Assay and Discovery of Small Molecules that Interrupt Malaria Transmission. *Cell host & microbe*.
35. Swann J, et al. (2016) High-Throughput Luciferase-Based Assay for the Discovery of Therapeutics That Prevent Malaria. *ACS Infect Dis* 2(4):281-293.
36. Yalaoui S, et al. (2008) Hepatocyte permissiveness to *Plasmodium* infection is conveyed by a short and structurally conserved region of the CD81 large extracellular domain. *PLoS pathogens* 4(2):e1000010.
37. Silvie O, et al. (2003) Hepatocyte CD81 is required for *Plasmodium falciparum* and *Plasmodium yoelii* sporozoite infectivity. *Nat Med* 9(1):93-96.
38. Scholz C, Knorr S, Hamacher K, & Schmidt B (2015) DOCKTITE—a highly versatile step-by-step workflow for covalent docking and virtual screening in the molecular operating environment. *Journal of chemical information and modeling* 55(2):398-406.

The invention claimed is:

1. A method for treating a disease or disorder associated with immune protease activity comprising:
administering to a subject in need thereof an effective amount of a composition comprising a carmaphycin B analog, wherein the carmaphycin B analog is (S)-2-((R)-2-hexanamido-3-(1H-indol-3-yl)propanamido)-N—((S)-4-methyl-1-((R)-2-methyloxiran-2-yl)-1-oxopentan-2-yl)hexanamide (Analog 19), and wherein the carmaphycin B analog has decreased cytotoxicity and increased selectivity for inhibiting immunoproteasome activity over constitutive proteasome activity as compared to carmaphycin B.

2. The method of claim 1, wherein the subject is a human.

3. The method of claim 1, wherein the disease is malaria.

4. The method of claim 1, wherein the disease is an immune related disorder.

5. The method of claim 1, wherein the disease is cancer.

6. The method of claim 1, wherein the disease is rheumatoid arthritis.

7. A pharmaceutical composition for treating a disease or disorder associated with immune protease activity comprising:
a carmaphycin B analog, wherein the carmaphycin B analog is (S)-2-((R)-2-hexanamido-3-(1H-indol-3-yl)propanamido)-N—((S)-4-methyl-1-((R)-2-methyloxiran-2-yl)-1-oxopentan-2-yl)hexanamide (Analog 19), and wherein the carmaphycin B analog has decreased cytotoxicity and increased selectivity for inhibiting immunoproteasome activity over constitutive proteasome activity as compared to carmaphycin B; and a pharmaceutically acceptable carrier.

* * * * *

SEQUENCE LISTING

<160> NUMBER OF SEQ ID NOS: 7

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Leu Leu Val Tyr
1

<210> SEQ ID NO 2
<211> LENGTH: 201
<212> TYPE: PRT
<213> ORGANISM: Homo sapiens

<400> SEQUENCE: 2

Thr Thr Thr Leu Ala Phe Lys Phe Arg His Gly Val Ile Val Ala Ala
1               5                   10                  15

Asp Ser Arg Ala Thr Ala Gly Ala Tyr Ile Ala Ser Gln Thr Val Lys
            20                  25                  30

Lys Val Ile Glu Ile Asn Pro Tyr Leu Leu Gly Thr Met Ala Gly Gly
        35                  40                  45

Ala Ala Asp Cys Ser Phe Trp Glu Arg Leu Leu Ala Arg Gln Cys Arg
    50                  55                  60

```
Ile Tyr Glu Leu Arg Asn Lys Glu Arg Ile Ser Val Ala Ala Ala Ser
 65                  70                  75                  80

Lys Leu Leu Ala Asn Met Val Tyr Gln Tyr Lys Gly Met Gly Leu Ser
                 85                  90                  95

Met Gly Thr Met Ile Cys Gly Trp Asp Lys Arg Gly Pro Gly Leu Tyr
            100                 105                 110

Tyr Val Asp Ser Glu Gly Asn Arg Ile Ser Gly Ala Thr Phe Ser Val
        115                 120                 125

Gly Ser Gly Ser Val Tyr Ala Tyr Gly Val Met Asp Arg Gly Tyr Ser
    130                 135                 140

Tyr Asp Leu Glu Val Glu Gln Ala Tyr Asp Leu Ala Arg Arg Ala Ile
145                 150                 155                 160

Tyr Gln Ala Thr Tyr Arg Asp Ala Tyr Ser Gly Gly Ala Val Asn Leu
                165                 170                 175

Tyr His Val Arg Glu Asp Gly Trp Ile Arg Val Ser Ser Asp Asn Val
            180                 185                 190

Ala Asp Leu His Glu Lys Tyr Ser Gly
        195                 200

<210> SEQ ID NO 3
<211> LENGTH: 211
<212> TYPE: PRT
<213> ORGANISM: Plasmodium falciparum

<400> SEQUENCE: 3

Thr Thr Thr Leu Ala Phe Lys Phe Lys Asp Gly Ile Ile Val Ala Val
 1               5                  10                  15

Asp Ser Arg Ala Ser Met Gly Ser Phe Ile Ser Ser Gln Asn Val Glu
                20                  25                  30

Lys Ile Glu Ile Asn Lys Asn Ile Leu Gly Thr Met Ala Gly Gly Gly
            35                  40                  45

Ala Ala Asp Cys Leu Tyr Trp Glu Lys Tyr Leu Gly Lys Ile Ile Lys
        50                  55                  60

Ile Tyr Glu Leu Arg Asn Asn Glu Lys Ile Ser Val Arg Ala Ala Ser
 65                  70                  75                  80

Thr Ile Leu Ser Asn Ile Leu Tyr Gln Tyr Lys Gly Tyr Gly Leu Cys
                 85                  90                  95

Cys Gly Ile Ile Leu Ser Gly Tyr Asp His Thr Gly Phe Asn Met Phe
            100                 105                 110

Tyr Val Asp Asp Ser Gly Lys Lys Val Glu Gly Asn Leu Phe Ser Cys
        115                 120                 125

Gly Ser Gly Ser Thr Tyr Ala Tyr Ser Ile Leu Asp Ser Ala Tyr Asp
    130                 135                 140

Tyr Asn Leu Asn Leu Asp Gln Ala Val Glu Leu Ala Arg Asn Ala Ile
145                 150                 155                 160

Tyr His Ala Thr Phe Arg Asp Gly Ser Gly Gly Lys Val Arg Val
                165                 170                 175

Phe His Ile His Lys Asn Gly Tyr Asp Lys Ile Ile Glu Gly Glu Asp
            180                 185                 190

Val Phe Asp Leu His Tyr His Tyr Thr Asn Pro Glu Gln Lys Asp Gln
        195                 200                 205

Tyr Val Met
210

<210> SEQ ID NO 4
```

<211> LENGTH: 212
<212> TYPE: PRT
<213> ORGANISM: Saccharomyces cerevisiae

<400> SEQUENCE: 4

```
Thr Thr Thr Leu Ala Phe Arg Phe Gln Gly Gly Ile Ile Val Ala Val
1               5                   10                  15

Asp Ser Arg Ala Thr Ala Gly Asn Trp Val Ala Ser Gln Thr Val Lys
            20                  25                  30

Lys Val Ile Glu Ile Asn Pro Phe Leu Leu Gly Thr Met Ala Gly Gly
        35                  40                  45

Ala Ala Asp Cys Gln Phe Trp Glu Thr Trp Leu Gly Ser Gln Cys Arg
    50                  55                  60

Leu His Glu Leu Arg Glu Lys Glu Arg Ile Ser Val Ala Ala Ala Ser
65                  70                  75                  80

Lys Ile Leu Ser Asn Leu Val Tyr Gln Tyr Lys Gly Ala Gly Leu Ser
                85                  90                  95

Met Gly Thr Met Ile Cys Gly Tyr Thr Arg Lys Glu Gly Pro Thr Ile
            100                 105                 110

Tyr Tyr Val Asp Ser Asp Gly Thr Arg Leu Lys Gly Asp Ile Phe Cys
        115                 120                 125

Val Gly Ser Gly Gln Thr Phe Ala Tyr Gly Val Leu Asp Ser Asn Tyr
    130                 135                 140

Lys Trp Asp Leu Ser Val Glu Asp Ala Leu Tyr Leu Gly Lys Arg Ser
145                 150                 155                 160

Ile Leu Ala Ala Ala His Arg Asp Ala Tyr Ser Gly Gly Ser Val Asn
                165                 170                 175

Leu Tyr His Val Thr Glu Asp Gly Trp Ile Tyr His Gly Asn His Asp
            180                 185                 190

Val Gly Glu Leu Phe Trp Lys Val Lys Glu Glu Gly Ser Phe Asn
        195                 200                 205

Asn Val Ile Gly
    210
```

<210> SEQ ID NO 5
<211> LENGTH: 213
<212> TYPE: PRT
<213> ORGANISM: Homo sapiens

<400> SEQUENCE: 5

```
Arg Phe Ser Pro Tyr Val Phe Asn Gly Gly Thr Ile Leu Ala Ile Ala
1               5                   10                  15

Gly Glu Asp Phe Ala Ile Val Ala Ser Asp Thr Arg Leu Ser Glu Gly
            20                  25                  30

Phe Ser Ile His Thr Arg Asp Ser Pro Lys Cys Tyr Lys Leu Thr Asp
        35                  40                  45

Lys Thr Val Ile Gly Cys Ser Gly Phe His Gly Asp Cys Leu Thr Leu
    50                  55                  60

Thr Lys Ile Ile Glu Ala Arg Leu Lys Met Tyr Lys His Ser Asn Asn
65                  70                  75                  80

Lys Ala Met Thr Thr Gly Ala Ile Ala Ala Met Leu Ser Thr Ile Leu
                85                  90                  95

Tyr Ser Arg Arg Phe Phe Pro Tyr Tyr Val Tyr Asn Ile Ile Gly Gly
            100                 105                 110

Leu Asp Glu Glu Gly Lys Gly Ala Val Tyr Ser Phe Asp Pro Val Gly
        115                 120                 125
```

Ser Tyr Gln Arg Asp Ser Phe Lys Ala Gly Gly Ser Ala Ser Ala Met
        130                 135                 140

Leu Gln Pro Leu Leu Asp Asn Gln Val Gly Phe Lys Asn Met Gln Asn
145                 150                 155                 160

Val Glu His Val Pro Leu Ser Leu Asp Arg Ala Met Arg Leu Val Lys
                165                 170                 175

Asp Val Phe Ile Ser Ala Ala Glu Arg Asp Val Tyr Thr Gly Asp Ala
            180                 185                 190

Leu Arg Ile Cys Ile Val Thr Lys Glu Gly Ile Arg Glu Glu Thr Val
        195                 200                 205

Ser Leu Arg Lys Asp
    210

<210> SEQ ID NO 6
<211> LENGTH: 240
<212> TYPE: PRT
<213> ORGANISM: Plasmodium falciparum

<400> SEQUENCE: 6

Met Asp Leu Ile Leu Tyr Asn Asp Asn Leu Thr Glu Lys Lys Thr Glu
1               5                   10                  15

Lys Glu Asn Val Ile Glu His Gly Arg Gly Phe Lys Arg Trp Tyr Pro
            20                  25                  30

Tyr Ile Asp Asn Gly Gly Thr Val Ile Gly Leu Thr Gly Lys Asp Tyr
        35                  40                  45

Val Ile Leu Ala Ala Asp Thr Arg Leu Ser Leu Ser Tyr Ser Ile Tyr
    50                  55                  60

Thr Arg Phe Cys Pro Lys Ile Ser Lys Leu Thr Asp Lys Cys Ile Ile
65                  70                  75                  80

Gly Ser Ser Gly Met Gln Ser Asp Ile Lys Thr Leu His Ser Leu Leu
                85                  90                  95

Gln Lys Lys Ile Gln Leu Phe Val Leu Glu His Ser His Tyr Pro Asp
            100                 105                 110

Ile His Val Ile Ala Arg Leu Leu Cys Val Ile Leu Tyr Ser Arg Arg
        115                 120                 125

Phe Phe Pro Tyr Tyr Ala Phe Asn Ile Leu Ala Gly Val Asp Glu Asn
    130                 135                 140

Asn Lys Gly Val Leu Tyr Asn Tyr Asp Ser Val Gly Ser Tyr Cys Glu
145                 150                 155                 160

Ala Thr His Ser Cys Val Gly Ser Gly Ser Gln Leu Ile Leu Pro Ile
                165                 170                 175

Leu Asp Asn Arg Val Glu Gln Lys Asn Gln Leu Ile Lys Asn Thr Asn
            180                 185                 190

Phe Asn Leu Gly Asp Asp Ile Asn Phe Val Lys Asp Ala Ile Thr Ser
        195                 200                 205

Ala Thr Glu Arg Asp Ile Tyr Thr Gly Asp Lys Thr Leu Ile Tyr Val
    210                 215                 220

Ile Asp Lys Met Gly Ile Asn Val Asn Thr Leu Asp Leu Lys Gln Asp
225                 230                 235                 240

<210> SEQ ID NO 7
<211> LENGTH: 222
<212> TYPE: PRT
<213> ORGANISM: Saccharomyces cerevisiae

<400> SEQUENCE: 7

```
Gln Phe Asn Pro Tyr Gly Asp Asn Gly Gly Thr Ile Leu Gly Ile Ala
1               5                   10                  15

Gly Glu Asp Phe Ala Val Leu Ala Gly Asp Thr Arg Asn Ile Thr Asp
                20                  25                  30

Tyr Ser Ile Asn Ser Arg Tyr Glu Pro Lys Val Phe Asp Cys Gly Asp
            35                  40                  45

Asn Ile Val Met Ser Ala Asn Gly Phe Ala Ala Asp Gly Asp Ala Leu
        50                  55                  60

Val Lys Arg Phe Lys Asn Ser Val Lys Trp Tyr His Phe Asp His Asn
65                  70                  75                  80

Asp Lys Lys Leu Ser Ile Asn Ser Ala Ala Arg Asn Ile Gln His Leu
                85                  90                  95

Leu Tyr Gly Lys Arg Phe Phe Pro Tyr Tyr Val His Thr Ile Ile Ala
                100                 105                 110

Gly Leu Asp Glu Asp Gly Lys Gly Ala Val Tyr Ser Phe Asp Pro Val
            115                 120                 125

Gly Ser Tyr Glu Arg Glu Gln Cys Arg Ala Gly Gly Ala Ala Ala Ser
        130                 135                 140

Leu Ile Met Pro Phe Leu Asp Asn Gln Val Asn Phe Lys Asn Gln Tyr
145                 150                 155                 160

Glu Pro Gly Thr Asn Gly Lys Val Lys Lys Pro Leu Lys Tyr Leu Ser
                165                 170                 175

Val Glu Glu Val Ile Lys Leu Val Arg Asp Ser Phe Thr Ser Ala Thr
                180                 185                 190

Glu Arg His Ile Gln Val Gly Asp Gly Leu Glu Ile Leu Ile Val Thr
            195                 200                 205

Lys Asp Gly Val Arg Lys Glu Phe Tyr Glu Leu Lys Arg Asp
210                 215                 220
```